(12) United States Patent
Feng et al.

(10) Patent No.: US 9,382,301 B2
(45) Date of Patent: Jul. 5, 2016

(54) TUBULIN-INTERACTING PROTEIN, CALTUBIN, PROMOTES AXONAL GROWTH

(71) Applicant: University of Toronto, Toronto (CA)

(72) Inventors: Zhong-Ping Feng, Toronto (CA); Nasrin Nejatbakhsh, Toronto (CA); Ronald E. Van Kesteren, Amsterdam (NL); August B. Smit, Amsterdam (NL); Hong-Shou Sun, Toronto (CA); Andrew Barszczyk, Toronto (CA)

(73) Assignee: University of Toronto, Toronto, ON, CA (US)

( * ) Notice: Subject to any disclaimer, the term of this patent is extended or adjusted under 35 U.S.C. 154(b) by 0 days.

(21) Appl. No.: 14/351,815

(22) PCT Filed: Oct. 12, 2012

(86) PCT No.: PCT/CA2012/000951
§ 371 (c)(1),
(2) Date: Apr. 14, 2014

(87) PCT Pub. No.: WO2013/053050
PCT Pub. Date: Apr. 18, 2013

(65) Prior Publication Data
US 2014/0329757 A1    Nov. 6, 2014

Related U.S. Application Data

(60) Provisional application No. 61/546,333, filed on Oct. 12, 2011.

(51) Int. Cl.
| | |
|---|---|
| *A01N 37/18* | (2006.01) |
| *A01N 57/00* | (2006.01) |
| *A61K 38/00* | (2006.01) |
| *C07K 14/435* | (2006.01) |
| *C07K 14/005* | (2006.01) |
| *C12N 7/00* | (2006.01) |

(52) U.S. Cl.
CPC ......... *C07K 14/43504* (2013.01); *C07K 14/005* (2013.01); *C12N 7/00* (2013.01); *C07K 2319/10* (2013.01); *C12N 2740/16033* (2013.01)

(58) Field of Classification Search
None
See application file for complete search history.

(56) References Cited

PUBLICATIONS

Nejatbakhsh, et al. "Caltubin, a Novel Molluscan Tubulin-Interacting Protein, Promotes Axonal Growth and Attenuates Axonal Degeneration of Rodent Neurons", J. Neurosci. Oct. 26, 2011.
Van Kesteren, et al., "Local Synthesis of Actin-Binding Protein β-Thymosin Regulates Neurite Outgrowth", J. Neurosci., Jan. 4, 2006.
Shintani, et al. "APC2 Plays an Essential Role in Axonal Projections through the Regulation of Microtubule Stability", J. Neurisci., Sep. 16m, 2009.

*Primary Examiner* — Olga N Chernyshev
(74) *Attorney, Agent, or Firm* — Cesari and McKenna, LLP

(57) ABSTRACT

A novel isolated protein, referred to herein as "caltubin", is provided. Caltubin promotes axonal regeneration, and prevents or at least reduces axonal retraction in neurons.

5 Claims, 12 Drawing Sheets

A  Caltubin protein sequence

```
MERAFEDVRSQHRDASLHNVLSRGTRSANGGVPCVTVPFL-40
TELKERFIRWLDHDNDGQSTFDEVKNYIRRFKPDVTDQTV-80
AAFISRRDSNGNGAIDFVPEYVHDMAAPDYTLEGANEWFK-120
LQDTNDDSFVTEAELVKVAEAVGMSPEEALDTVQGYYMSA-160
DANKDGKLSLDEFKTLYSP    (SEQ ID NO: 18)
```

B  Nucleotide sequence

```
  1 ATGGAGAGGGCCTTCGAGGACGTCAGGAGTCAGCACAGGGACGCGTCACTGCACAACGTG
 61 CTGAGCAGGGGCACCCGGAGCGCCAATGGCGGCGTGCCATGCGTGACCGTTCCATTTTTA
121 ACAGAACTGAAGGAGCGCTTCATCCGCTGGCTGGACCACGACAACGACGGCCAGTCCACG
181 TTCGACGAGGTCAAGAACTACATCAGACGCTTTAAGCCTGACGTCACGGACCAGACGGTG
241 GCCGCTTTCATCAGTCGCCGAGACAGCAACGGGAACGGCGCCATAGACTTCGTCCCCGAG
301 TACGTCCACGACATGGCGGCACCAGACTACACGCTCGAGGGCGCCAACGAGTGGTTTAAA
361 CTCCAGGACACCAACGATGACAGCTTTGTAACAGAGGCAGAGCTGGTCAAGGTGGCAGAG
421 GCTGTCGGCATGTCCCCAGAGGAGGCACTGGACACTGTCCAGGGTTATTACATGTCCGCC
481 GATGCGAACAAGGACGGGAAACTTTCACTTGATGAATTCAAGACACTGTACAGCCCT
```
(SEQ ID NO: 19)

FIGURE 1

A
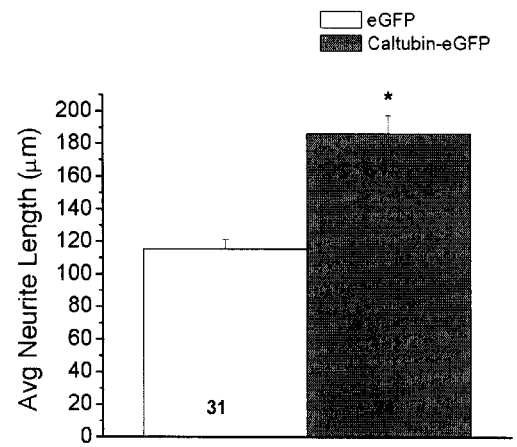
B
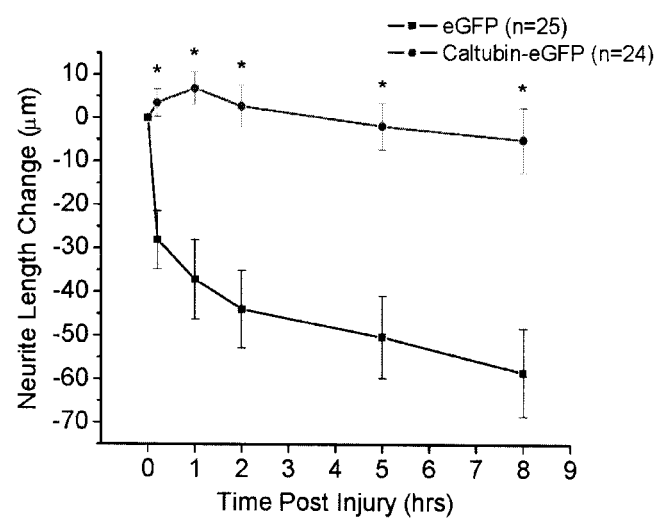
FIGURE 8

Sequences of caltubin and truncated caltubin peptides conjugated with cell-penetrating arginine-enriched domain

Full Length Caltubin-Tat

His Tag — Thrombin Cleavage Site — Caltubin — HIV Tat Cell Penetrating Domain

MAHHHHHHVDDDDKMLVPRGSGAMERAFEDVRSQHRDASLHNVLSRGTRSAN
GGVPCVTVPFLTELKERFIRWLDHDNDGQSTFDEVKNYIRRFKPDVTDQTVAAFISR
RDSNGNGAIDFVPEYVHDMAAPDYTLEGANEWFKLQDTNDDSFVTEAELVKVAE
AVGMSPEEALDTVQGYYMSADANKDGKLSLDEFKTLYSPAAYGRKKRRQRRR

SEQ. ID. NO.:26

N-terminal Caltubin-Tat

His Tag — Thrombin Cleavage Site — Caltubin — HIV Tat Cell Penetrating Domain

MAHHHHHHVDDDDKMLVPRGSGAMERAFEDVRSQHRDASLHNVLSRGTRSAN
GGVPCVTVPFLTELKERFIRWLDHDNDGQSTFDEVKNYIRRFKPDVTDQTVAAFISR
RDSNGNGAIDFVPEYVHDMAAPDYTLAAYGRKKRRQRRR

SEQ. ID. NO.:27

C-terminal Caltubin-Tat

His Tag — Thrombin Cleavage Site — Caltubin — HIV Tat Cell Penetrating Domain

MAHHHHHHVDDDDKMLVPRGSGAEGANEWFKLQDTNDDSFVTEAELVKVAEA
VGMSPEEALDTVQGYYMSADANKDGKLSLDEFKTLYSPAAYGRKKRRQRRR

SEQ. ID. NO.:28

FIGURE 10B

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ttgtaacaga ggcagagctg                                              20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
agtttcccgt ccttgttcg                                               19

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
ctgtgagcca tcaagctgtt g                                            21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ggtgtacatg gcatccgatt t                                            21

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
```
agccatcctt cttgggtatg                                              20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
agtttcccgt ccttgttcg                                               19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
agccatcctt cttgggtatg                                              20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
atacctggga acatggtggt                                              20

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
accttgactg tgctaaggta gcataa                                       26

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
cagttcttcc ctattaatcc gttcat                                       26

<210> SEQ ID NO 11
<211> LENGTH: 25
<212> TYPE: RNA
<213> ORGANISM: Artificial Sequence
<220> FEATURE:
<223> OTHER INFORMATION: siRNA sequence

<400> SEQUENCE: 11
gaaacuuuca cuugaugaau ucaag                                        25

<210> SEQ ID NO 12
<211> LENGTH: 25
<212> TYPE: RNA
<213> ORGANISM: Artificial Sequence

```
<220> FEATURE:
<223> OTHER INFORMATION: siRNA sequence

<400> SEQUENCE: 12
ccacguucga cgaggucaag aacua                                              25

<210> SEQ ID NO 13
<211> LENGTH: 25
<212> TYPE: RNA
<213> ORGANISM: Artificial Sequence
<220> FEATURE:
<223> OTHER INFORMATION: siRNA

<400> SEQUENCE: 13
uggacacugu ccaggguuau uacau                                              25

<210> SEQ ID NO 14
<211> LENGTH: 25
<212> TYPE: RNA
<213> ORGANISM: Artificial Sequence
<220> FEATURE:
<223> OTHER INFORMATION: siRNA

<400> SEQUENCE: 14
uuaaugaugc cauugguuag auaua                                              25

<210> SEQ ID NO 15
<211> LENGTH: 27
<212> TYPE: RNA
<213> ORGANISM: Artificial Sequence
<220> FEATURE:
<223> OTHER INFORMATION: siRNA

<400> SEQUENCE: 15
ucacaaggga gagaaagaga ggaagga                                            27

<210> SEQ ID NO 16
<211> LENGTH: 15
<212> TYPE: PRT
<213> ORGANISM: Artificial Sequence
<220> FEATURE:
<223> OTHER INFORMATION: synthetic peptide

<400> SEQUENCE: 16

Met Glu Arg Ala Phe Glu Asp Val Arg Ser Gln His Arg Asp Cys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: synthetic peptide

<400> SEQUENCE: 17

Cys Asp Gly Lys Leu Ser Leu Asp Glu Phe Lys Thr Leu Tyr Ser Pro
1               5                   10                  15

<210> SEQ ID NO 18
<211> LENGTH: 179
<212> TYPE: PRT
<213> ORGANISM: snail

<400> SEQUENCE: 18

Met Glu Arg Ala Phe Glu Asp Val Arg Ser Gln His Arg Asp Ala Ser
1               5                   10                  15
```

```
Leu His Asn Val Leu Ser Arg Gly Thr Arg Ser Ala Asn Gly Gly Val
             20                  25                  30

Pro Cys Val Thr Val Pro Phe Leu Thr Glu Leu Lys Glu Arg Phe Ile
         35                  40                  45

Arg Trp Leu Asp His Asp Asn Asp Gly Gln Ser Thr Phe Asp Glu Val
 50                  55                  60

Lys Asn Tyr Ile Arg Arg Phe Lys Pro Asp Val Thr Asp Gln Thr Val
 65                  70                  75                  80

Ala Ala Phe Ile Ser Arg Arg Asp Ser Asn Gly Asn Gly Ala Ile Asp
                 85                  90                  95

Phe Val Pro Glu Tyr Val His Asp Met Ala Ala Pro Tyr Thr Leu
             100                 105                 110

Glu Gly Ala Asn Glu Trp Phe Lys Leu Gln Asp Thr Asn Asp Asp Ser
         115                 120                 125

Phe Val Thr Glu Ala Glu Leu Val Lys Val Ala Glu Ala Val Gly Met
 130                 135                 140

Ser Pro Glu Glu Ala Leu Asp Thr Val Gln Gly Tyr Tyr Met Ser Ala
145                 150                 155                 160

Asp Ala Asn Lys Asp Gly Lys Leu Ser Leu Asp Glu Phe Lys Thr Leu
                165                 170                 175

Tyr Ser Pro

<210> SEQ ID NO 19
<211> LENGTH: 537
<212> TYPE: DNA
<213> ORGANISM: snail

<400> SEQUENCE: 19
atggagaggg ccttcgagga cgtcaggagt cagcacaggg acgcgtcact gcacaacgtg      60
ctgagcaggg gcacccggag cgccaatggc ggcgtgccat gcgtgaccgt tccatttta     120 acagaactga aggagcgctt catccgctgg ctggaccaca caacgacgg ccagtccacg     180 ttcgacgagg tcaagaacta catcagacgc tttaagcctg acgtcacgga ccagacggtg     240
gccgctttca tcagtcgccg agacagcaac gggaacggcg ccatagactt cgtccccgag     300
tacgtccacg acatggcggc accagactac acgctcgagg gcgccaacga gtggtttaaa     360
ctccaggaca ccaacgatga cagctttgta acagaggcag agctggtcaa ggtggcagag     420
gctgtcggca tgtccccaga ggaggcactg gacactgtcc agggttatta catgtccgcc     480
gatgcgaaca aggacgggaa actttcactt gatgaattca agacactgta cagccct        537

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
gacgacgaca agatgctggt tcctcgtggt tgg                                    33

<210> SEQ ID NO 21
<211> LENGTH: 34
<212> TYPE: DNA
<213> ORGANISM: Artificial Sequence
<220> FEATURE:
<223> OTHER INFORMATION: primer
```

<400> SEQUENCE: 21
gaggagaagc cggttagcga cgacgtttct tacg                                34

<210> SEQ ID NO 22
<211> LENGTH: 8
<212> TYPE: PRT
<213> ORGANISM: Artificial Sequence
<220> FEATURE:
<223> OTHER INFORMATION: His-6 tag

<400> SEQUENCE: 22

Met Ala His His His His His His
1               5

<210> SEQ ID NO 23
<211> LENGTH: 7
<212> TYPE: PRT
<213> ORGANISM: Artificial Sequence
<220> FEATURE:
<223> OTHER INFORMATION: linker region

<400> SEQUENCE: 23

Val Asp Asp Asp Asp Lys Met
1               5

<210> SEQ ID NO 24
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 24

Leu Val Pro Arg Gly Ser
1               5

<210> SEQ ID NO 25
<211> LENGTH: 11
<212> TYPE: PRT
<213> ORGANISM: Artificial Sequence
<220> FEATURE:
<223> OTHER INFORMATION: HIV TAT protein transduction domain

<400> SEQUENCE: 25

Tyr Gly Arg Lys Lys Arg Arg Gln Arg Arg
1               5                   10

<210> SEQ ID NO 26
<211> LENGTH: 215
<212> TYPE: PRT
<213> ORGANISM: Artificial Sequence
<220> FEATURE:
<223> OTHER INFORMATION: caltubin-TAT protein

<400> SEQUENCE: 26

Met Ala His His His His His His Val Asp Asp Asp Lys Met Leu
1               5                   10                  15

Val Pro Arg Gly Ser Gly Ala Met Glu Arg Ala Phe Glu Asp Val Arg
            20                  25                  30

Ser Gln His Arg Asp Ala Ser Leu His Asn Val Leu Ser Arg Gly Thr
            35                  40                  45

Arg Ser Ala Asn Gly Gly Val Pro Cys Val Thr Val Pro Phe Leu Thr
        50                  55                  60

Glu Leu Lys Glu Arg Phe Ile Arg Trp Leu Asp His Asp Asn Asp Gly

```
                 65                  70                  75                  80
Gln Ser Thr Phe Asp Glu Val Lys Asn Tyr Ile Arg Arg Phe Lys Pro
                 85                  90                  95

Asp Val Thr Asp Gln Thr Val Ala Ala Phe Ile Ser Arg Arg Asp Ser
                100                 105                 110

Asn Gly Asn Gly Ala Ile Asp Phe Val Pro Glu Tyr Val His Asp Met
                115                 120                 125

Ala Ala Pro Asp Tyr Thr Leu Glu Gly Ala Asn Glu Trp Phe Lys Leu
                130                 135                 140

Gln Asp Thr Asn Asp Asp Ser Phe Val Thr Glu Ala Glu Leu Val Lys
145                 150                 155                 160

Val Ala Glu Ala Val Gly Met Ser Pro Glu Glu Ala Leu Asp Thr Val
                165                 170                 175

Gln Gly Tyr Tyr Met Ser Ala Asp Ala Asn Lys Asp Gly Lys Leu Ser
                180                 185                 190

Leu Asp Glu Phe Lys Thr Leu Tyr Ser Pro Ala Ala Tyr Gly Arg Lys
                195                 200                 205

Lys Arg Arg Gln Arg Arg
            210                 215

<210> SEQ ID NO 27
<211> LENGTH: 36
<212> TYPE: PRT
<213> ORGANISM: Artificial Sequence
<220> FEATURE:
<223> OTHER INFORMATION: N-terminal caltubin-TAT

<400> SEQUENCE: 27

Met Ala His His His His His His Val Asp Asp Asp Lys Met Leu
1               5                   10                  15

Val Pro Arg Gly Ser Gly Ala Ala Ala Tyr Gly Arg Lys Lys Arg Arg
                20                  25                  30

Gln Arg Arg Arg
            35

<210> SEQ ID NO 28
<211> LENGTH: 103
<212> TYPE: PRT
<213> ORGANISM: Artificial Sequence
<220> FEATURE:
<223> OTHER INFORMATION: C-terminal caltubin-TAT

<400> SEQUENCE: 28

Met Ala His His His His His His Val Asp Asp Asp Lys Met Leu
1               5                   10                  15

Val Pro Arg Gly Ser Gly Ala Glu Gly Ala Asn Glu Trp Phe Lys Leu
                20                  25                  30

Gln Asp Thr Asn Asp Asp Ser Phe Val Thr Glu Ala Glu Leu Val Lys
            35                  40                  45

Val Ala Glu Ala Val Gly Met Ser Pro Glu Glu Ala Leu Asp Thr Val
        50                  55                  60

Gln Gly Tyr Tyr Met Ser Ala Asp Ala Asn Lys Asp Gly Lys Leu Ser
65                  70                  75                  80

Leu Asp Glu Phe Lys Thr Leu Tyr Ser Pro Ala Ala Tyr Gly Arg Lys
                85                  90                  95

Lys Arg Arg Gln Arg Arg
            100
```

TUBULIN-INTERACTING PROTEIN, CALTUBIN, PROMOTES AXONAL GROWTH

CROSS-REFERENCE TO RELATED APPLICATIONS

This application is the National Stage of International Application No. PCT/CA2012/000951, filed on Oct. 12, 2012, which claims the benefit U.S. Provisional Application No. 61/546,333, filed on Oct. 12, 2012. The contents of both applications are hereby incorporated by reference in their entirety.

FIELD OF THE INVENTION

The present invention relates generally to the treatment nerve injury, and more particularly, to a novel protein that is useful to treat nerve injury in the mammalian nervous system.

BACKGROUND OF THE INVENTION

Whereas adult mammalian peripheral neurons retain the capacity to regenerate injured axons, central mammalian neurons are severely limited in their regenerative growth capacity. The inability of central neurons to regenerate injured axons is due to both extrinsic and intrinsic factors. Extracellular inhibitory molecules (e.g. Nogo, MAG and OMgp) limit regeneration in the mature central nervous system (CNS). However, genetic deletion of these inhibitory molecules is insufficient for successful axonal regeneration. Manipulation of intrinsic neuronal processes can overcome these extrinsic inhibitory signals, and promote axon regeneration both in vitro and in vivo. Thus, understanding neuron-intrinsic mechanisms of axon regeneration is pivotal in the development of treatments for traumatic brain injury, spinal cord injuries, and neurodegenerative disorders.

In contrast to mature mammalian neurons, adult central neurons of some lower vertebrates and most invertebrates spontaneously regenerate following axonal injury. For instance, adult neurons of the freshwater snail *Lymnaea stagnalis* (*L. stagnalis*) have the capacity to regenerate their injured axons and re-form cell-type specific synapses, both in vitro, and in vivo. Invertebrate neurons and peripheral mammalian neurons share the capacity to locally synthesize proteins in axons and growth cones, and the identification of locally synthesized proteins has provided valuable insights into mechanisms of axon outgrowth and regeneration. Approximately 100-200 local transcripts have been reported in isolated neurites of various neuronal preparations, e.g., in Aplysia sensory neurons, in squid axoplasm and in vertebrate axons. Many of the local transcripts encode cytoskeletal proteins (e.g., microtubule, microfilament, and intermediate filament proteins), or proteins that regulate cytoskeletal dynamics (e.g., Rho and β-thymosin), suggesting that regulation of the cytoskeleton through local protein synthesis potentially serves as a conserved mechanism underlying axonal outgrowth and regeneration.

Given the need in the art for effective methods of treating nerve injury, it would be desirable to identify novel means of enhancing nerve growth and/or promoting nerve regeneration.

SUMMARY OF THE INVENTION

A novel protein has now been identified which is effective to treat nerve injury. The novel protein has been determined to promote axonal regeneration in neurons, and to attenuate axonal degeneration in neurons following injury.

Thus, in one aspect of the invention, a novel isolated protein, referred to herein as caltubin, is provided, along with nucleotides encoding caltubin and vectors expressing incorporating such nucleotides.

In another aspect of the invention, a method of promoting axonal regeneration in neurons is provided comprising administering a therapeutically effective amount of caltubin, a functionally equivalent variant thereof or a nucleic acid expressing caltubin or variant thereof to neurons.

In another aspect, a method of preventing, or at least reducing, axonal retraction in neurons is provided comprising administering a therapeutically effective amount of caltubin, a functionally equivalent variant thereof or a nucleic acid expressing caltubin or variant thereof to neurons.

In a further aspect, a method of treating a neurodegenerative disorder in a mammal is provided comprising administering a therapeutically effective amount of caltubin, a peptide thereof or a nucleic acid expressing caltubin to the mammal.

These and other aspects of the invention will become apparent in the detailed description that follows by reference to the following figures.

BRIEF DESCRIPTION OF THE FIGURES

FIG. 1 illustrates the amino acid (A) and nucleic acid (B) sequences of caltubin;

FIG. 8 graphically illustrates that caltubin expression in mouse primary cortical neurons promotes axonal elongation (A) and attenuates axonal retraction (B);

DETAILED DESCRIPTION OF THE INVENTION

Figure 2:
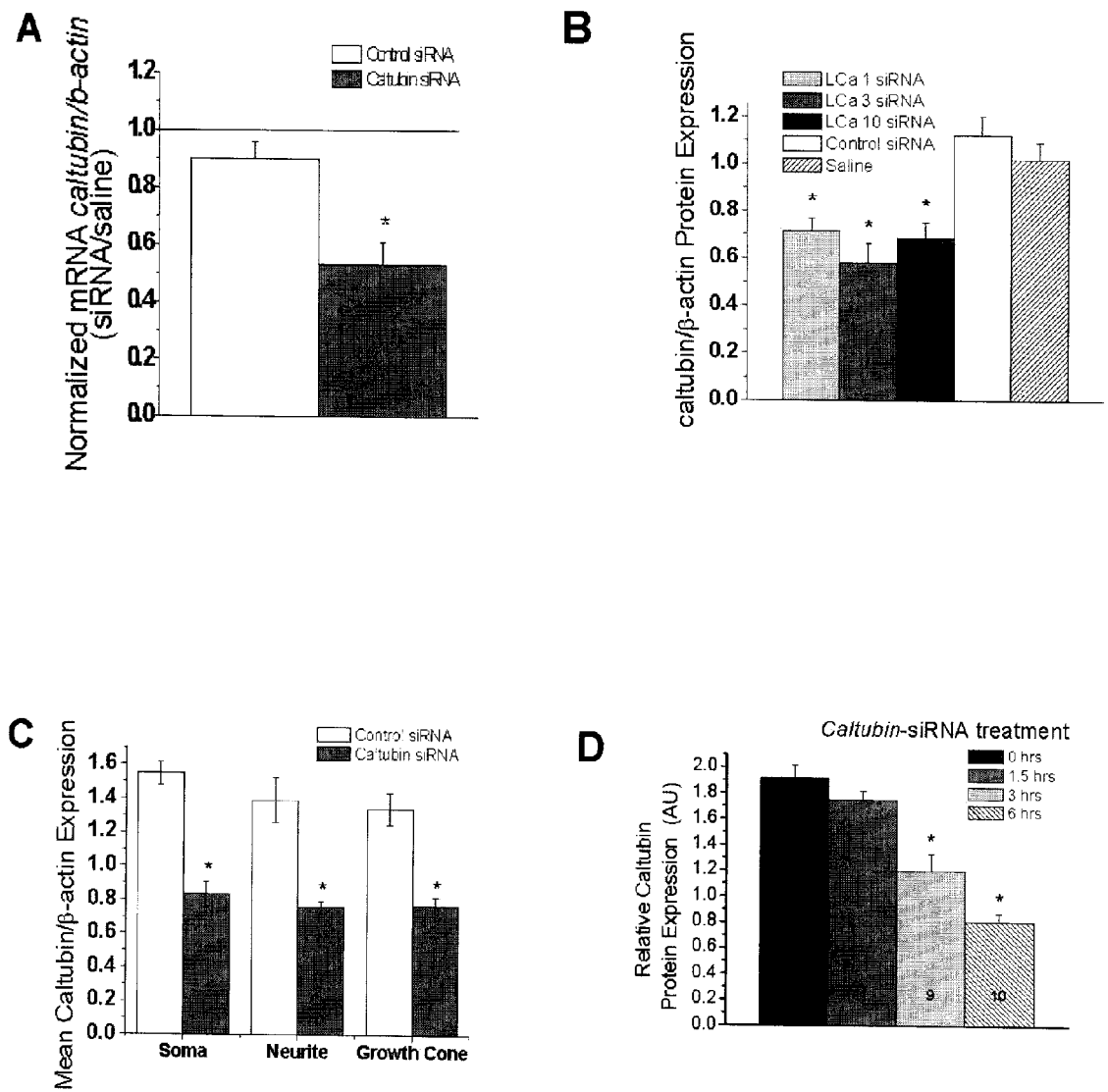
FIG. 2 graphically illustrates that caltubin-specific siRNAs effectively knocked down caltubin mRNA (A) and protein levels (B) in intact ganglia in vivo and in cultured PeA neurons in vitro (FIG. 2C/D)

A novel isolated protein, referred to herein as caltubin, is provided. Caltubin exhibits nerve healing activity, including axon-regenerating activity and/or prevention or at least reduction of axon retraction in injured neurons.

As used herein, "caltubin" refers to a tubulin-interacting protein that exhibits nerve healing, e.g. axon-regenerating activity and/or prevention of axon retraction. In one embodiment, caltubin is encoded by the nucleic acid sequence shown in FIG. 9A, or a functionally equivalent nucleic acid sequence which varies therefrom, for example, as a result of codon degeneracy, and has the amino acid sequence as set out in FIG. 9B. As one of skill in the art will appreciate, functionally equivalent caltubin variants and polynucleotides encoding such variants, are also encompassed, including analogues, fragments and derivatives thereof, which vary in amino acid sequence but which retain tubulin-interacting and axon-regenerating activity. Caltubin and functionally equivalent variants thereof are collectively encompassed by the term "caltubin protein".

The term "isolated" as used herein with respect to caltubin, variants thereof, and polynucleotides encoding such proteins, refers to caltubin proteins and polynucleotides that are essentially free from cellular components with which they are generally associated in vivo.

The term "functionally equivalent variants" as used herein with respect to caltubin includes naturally and non-naturally occurring variants of caltubin that retain activity, e.g. axon-regenerating activity and/or prevention of axon retraction. The variant need not exhibit identical activity to caltubin, but will exhibit sufficient activity to render it useful for nerve healing, e.g. at least about 25% of the activity of caltubin, and preferably at least about 50% or greater of the activity of caltubin. Such functionally equivalent variants may result naturally from species differences, alternative splicing during transcription or from genetic coding differences and may retain significant sequence homology with caltubin, e.g. at least about 80% sequence homology, preferably at least about 85% sequence homology, and more preferably at least about 90% or greater sequence homology. Such variants may readily be identified using established cloning techniques employing primers derived from caltubin. Additionally, such modifications may result from non-naturally occurring synthetic alterations made to caltubin to render functionally equivalent variants which having more desirable characteristics for use in a therapeutic sense, for example, increased activity or stability. Functionally equivalent variants, thus, include analogues, fragments and derivatives thereof.

A functionally equivalent analogue of caltubin in accordance with the present invention, either naturally or non-naturally-occurring analogues, may incorporate one or more amino acid substitutions, additions or deletions, either internally or terminally. Examples of suitable amino acid substitutions, additions or deletions include those incurred at positions within the protein that are not closely linked to activity, e.g. tubulin interaction, such as within the C-terminal region (amino acid residues 337-537). Conservative amino acid substitutions within caltubin may also generate functionally equivalent analogues thereof. Examples of conservative substitutions include the substitution of a non-polar (hydrophobic) residue such as alanine, isoleucine, valine, leucine or methionine with another non-polar (hydrophobic) residue; the substitution of a polar (hydrophilic) residue with another such as between arginine and lysine, between glutamine and asparagine, between glutamine and glutamic acid, between asparagine and aspartic acid, and between glycine and serine; the substitution of a basic residue such as lysine, arginine or histidine with another basic residue; or the substitution of an acidic residue, such as aspartic acid or glutamic acid with another acidic residue.

A functionally equivalent caltubin fragment in accordance with the present invention comprises a portion of a caltubin sequence which retains at least some function of intact caltubin, for example, N-terminal caltubin peptides comprising sufficient amino acid residues from the N-terminus which retain tubulin-interacting and axon-regenerating activity. Suitable N-terminal caltubin peptides, for example, may comprise any fragment of residues from the caltubin N-terminus, e.g. from residues 1-150. Suitable fragments, thus, may comprise, amino acids residues from the N-terminal end of the protein, for example, N-terminal residues 1-50, and preferably comprise residues 1-60, 1-70, 1-80, 1-90, 1-100, 1-110, 1-120 and so on. In one embodiment, the N-terminal caltubin fragment including residues 1-112 was found to exhibit caltubin activity. Alternatively, fragments within the N-terminus which begin at residues other than the first amino acid of the caltubin and which retain activity are also within the scope of the present invention, for example, a fragment from within residues 110-150, residues 80-150, residues 20 or 30 to 120-150, and so on.

A functionally equivalent derivative of caltubin in accordance with the present invention is caltubin, or an analogue or fragment thereof, in which one or more of the amino acid residues therein is chemically derivatized. The amino acids may be derivatized at the amino or carboxy groups, or alternatively, at the side "R" groups thereof. Derivatization of amino acids within the peptide may render a peptide having more desirable characteristics such as increased stability or activity. Such derivatized molecules include for example, those molecules in which free amino groups have been derivatized to form, for example, amine hydrochlorides, p-toluene sulfonyl groups, carbobenzoxy groups, t-butyloxycarbonyl groups, chloroacetyl groups or formyl groups. Free carboxyl groups may be derivatized to form, for example, salts, methyl and ethyl esters or other types of esters or hydrazides. Free hydroxyl groups may be derivatized to form, for example, O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids, for example: 4-hydroxyproline may be substituted for proline; 5-hydroxylysine may be substituted for lysine; 3-methylhistidine may be substituted for histidine; homoserine may be substituted for serine; and ornithine may be substituted for lysine. Terminal derivatization of the protein to protect against chemical or enzymatic degradation is also encompassed including acetylation at the N-terminus and amidation at the C-terminus of the peptide.

Caltubin, and functionally equivalent variants thereof, i.e. caltubin proteins, may be made using standard, well-established solid-phase peptide synthesis methods (SPPS). Two methods of solid phase peptide synthesis include the BOC and FMOC methods. Caltubin proteins may also be made using any one of a number of suitable techniques based on recombinant technology. It will be appreciated that such techniques are well-established in the art, and involve the expression of periostin-encoding nucleic acid in a genetically engineered host cell. DNA encoding a caltubin protein may be synthesized de novo by automated techniques also well-known in the art.

Once prepared and suitably purified, caltubin or a functionally equivalent variant thereof, may be utilized in accordance with the invention for nerve healing. In this regard, increasing the expression of caltubin at a target site including neurons, by administration of a caltubin protein or by administration of caltubin-encoding nucleic acid, results in caltubin expression or over-expression at a target site including neurons to promote nerve regeneration via axon regrowth and/or prevent axon retraction.

Administration of caltubin, or functionally equivalent variant thereof, either alone or in combination with at least one pharmaceutically acceptable adjuvant, may be used to treat nerve injury in accordance with the invention. The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with peptide-based drugs, such as diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, anti-oxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered, for example, anti-microbial agents may be added to the composition to prevent microbial growth over prolonged storage periods.

To increase the efficiency of caltubin delivery into cells, the caltubin protein may be linked to a cell-penetrating protein or peptide. Examples of suitable cell-penetrating peptides include, but are not limited to, arginine/guanidine-rich peptides, including for example, the HIV-TAT peptides and derivatives thereof, vascular endothelial-cadherin, transportan, penetratin, Pep-1 peptides and fragments thereof. Linkage of a cell-penetrating protein to a caltubin protein may be accomplished using well-established techniques, such as those described in the specific examples herein.

Caltubin, and functionally equivalent variants thereof, may also be coated or encased in a protective material to prevent undesirable degradation by, for example, enzymes, acids or other conditions that may affect the therapeutic activity thereof on administration. Such coatings are formulated to release the active protein at an appropriate time following administration, and include sustained-release coatings prepared from appropriate material, such as polymer coatings, gelatin, liposomes and the like.

Caltubin, and functionally equivalent variants thereof, are useful to promote axonal regeneration in neurons, and/or to prevent or at least reduce axonal retraction in injured neurons. Thus, caltubin is useful to treat injury in nerve cells, as well as conditions involving nerve injury or degeneration, such as, but not limited to, peripheral nerve injury, traumatic brain injury and spinal cord injury, as well as neurodegenerative disorders such as Alzheimer's disease, Huntington's disease, Parkinson's disease and Amyotrophic lateral sclerosis (ALS), stroke and optical nerve degeneration or injury.

Thus, in another aspect of the invention, a method of treating nerve injury or degeneration in mammalian cells and within a mammal is provided. The terms "treat", "treating" and "treatment" are used broadly herein to denote methods that favorably alter the targeted condition, including those that moderate or reverse the progression of, reduce the severity or symptoms thereof, or prevent or cure the target condition. The method comprises administering a therapeutically effective amount of caltubin, or a functionally equivalent variant thereof, or a caltubin-encoding nucleic acid, to cells or to the mammal. As used herein, the term "mammal" is meant to encompass, without limitation, humans and non-human mammals including domestic animals such as dogs, cats, horses, cattle, swine, sheep, goats and the like, as well as non-domesticated animals. The term "therapeutically effective amount" is an amount of caltubin required to induce axon regeneration or prevent axon retraction while not exceeding an amount which may cause significant adverse effects. Dosages of caltubin, or functionally equivalent variants thereof, that are therapeutically effective will vary with many factors including the nature of the condition being treated as well as the particular mammal being treated, the mode of administration and the dosage form used. In one embodiment, dosages within the range of about 0.01 mg/kg to about 10 mg/kg may be utilized.

The caltubin, or functionally equivalent variant thereof, is administered in a suitable dosage form based on the mode of administration. As one of skill in the art will appreciate, caltubin may be administered by any of a number of routes including but not limited to oral, subcutaneous, intravenous, intraperitoneal, intranasal, enteral, topical, sublingual, intramuscular, intra-arterial, intramedullary, intrathecal, inhalation, ocular, transdermal, vaginal or rectal means. Caltubin protein or peptides may also be administered to cells in ex vivo treatment protocols.

In an alternative method, caltubin-encoding nucleic acid molecules or polynucleotides may administered to a mammal to treat nerve injury or degeneration. In this regard, it is expected that administration of a caltubin-encoding oligonucleotide to a mammal in an amount that results in expression of at least about 0.01 mg/kg to about 10 mg/kg caltubin protein will be suitable to treat nerve injury or degeneration.

The term "oligonucleotide" or "polynucleotide" refers to an oligomer or polymer of nucleotide or nucleoside monomers consisting of naturally occurring bases, sugars, and intersugar (backbone) linkages. The term also includes modified or substituted oligonucleotides comprising non-naturally occurring monomers or portions thereof, which function similarly. Such modified or substituted oligonucleotides may be preferred over naturally occurring forms in view of enhanced cellular uptake, or increased stability in the presence of nucleases. The term also includes chimeric oligonucleotides which contain two or more chemically distinct regions. For example, chimeric oligonucleiotides may contain at least one region of modified nucleotides that confer beneficial properties (e.g. increased nuclease resistance, increased uptake into cells), or two or more oligonucleotides of the invention may be joined to form a chimeric oligonucleotide. Other oligonucleotides of the invention may contain modified phosphorous, oxygen heteroatoms in the phosphate backbone, short chain alkyl or cycloalkyl intersugar linages or short chain heteroatomic or heterocyclic intersugar linkages. For example, oligonucleotides may contain phosphorothioates, phosphotriesters, methyl phosphonates, and phophorodithioates. Oligonucleotides of the invention may also comprise nucleotide analogs such as peptide nucleic acid (PNA) in which the deoxribose (or ribose) phosphate backbone in the DNA (or RNA), is replaced with a polymide backbone similar to that found in peptides. Other oligonucleotide analogues may contain nucleotides containing polymer backbones, cyclic backbones, or acyclic backbones, e.g. morpholino backbone structures.

Such oligonucleotide molecules are readily synthesized using procedures known in the art based on the available sequence information. For example, oligonucleotides may be chemically synthesized using naturally occurring nucleotides or modified nucleotides as described above designed to increase the biological stability of the molecules or to increase the physical stability of the duplex formed with mRNA or the native gene, e.g. phosphorothioate derivatives and acridine substituted nucleotides. Selected oligonucleotides may also be produced biologically using recombinant technology in which an expression vector, e.g. plasmid, phagemid or attenuated virus, is introduced into cells in which the oligonucleotide is produced under the control of a regulatory region.

Once prepared, caltubin-encoding oligonucleotides may be introduced into tissues or cells, e.g. such as cells removed from the mammal, using techniques in the art including, for example, introduction via vector (retroviral vectors, adenoviral vectors and DNA virus vectors) or introduction using physical techniques such as microinjection. Thus, therapeutic oligonucleotides may be directly administered in vivo or may be used to transfect cells in vitro which are then administered in vivo.

Embodiments of the invention are described by reference to the following specific examples which are not to be construed as limiting.

EXAMPLE 1

Materials and Methods

Animals. Freshwater snails, *L. stagnalis* (a hermaphrodite), were kept in water at 20° C. under a 12/12 h light/dark cycle, and fed green leaf lettuce twice a week. Adult snails with shell lengths of 15-20 mm were used. All experiments were carried out according to the guidelines of the Animal Care Committee of the University of Toronto.

Primary cell culture and cell isolation. Snails were anaesthetized with 10% (v/v) Listerine for 10 min as previously described (Hui et al., 2007). Central ganglia were dissected out in sterile snail saline containing (in mM): NaCl, 51.3; KCl, 1.7; $CaCl_2$, 4.1; $MgCl_2$, 1.5 (pH was adjusted to 7.9 with 1 M HEPES/NaOH) and incubated with 3 mg/ml trypsin (Type III, Sigma, ON, Canada) for 20 min. Neurons were placed in poly-l-lysine-coated culture dishes and maintained in conditioned medium (CM) (Feng et al., 1997) at room temperature. Anisomycin (A9789, Sigma), a protein synthesis inhibitor which acts by inhibiting peptidyl transferase activity, was added to culture media at various concentrations as previously described (Roche et al., 2009).

In situ hybridization. Cultured neurons were fixed in 1% paraformaldehyde/1% acetic acid and permeabilized with 0.5% NP-40. Brains were fixed in 1% paraformaldehyde/1% acetic acid and embedded in paraffin, and 7 μm sections were adhered to 0.5% gelatin/0.5% chromalum-coated slides. Digoxigenin-labeled run-off sense and antisense RNA were synthesized from linearized pBluescript plasmids using T3 or T7 RNA polymerase and a dioxigenin-UTP labeling mixture (both from Roche Diagnostics, Mannheim, Germany). In situ hybridizations were performed as described previously (Smit et al., 1996).

Real-time Quantitative PCR (qPCR). PeA neurons were cultured (8-10 cells per dish) for 2 days. RNA was isolated from the transacted neurites and from the corresponding somata separately. After removal of DNA by DNase I treatment, the RNA was random primed with 300 μmol of random hexanucleotides and reverse transcribed into cDNA. qPCR was performed in triplicate on each cDNA sample using an ABI PRISM 7700 Sequence Detection System (Applied Biosystems, Foster City, Calif.) with SYBR Green as the reporter dye. All reactions were performed according to the instructions of the manufacturer. The following primers were used: caltubin (forward: 5'-TTGTAACAGAGGCAGAGC-TG-3' (SEQ ID NO: 1); reverse: 5'-AGTTTCCCGTCCTTGTTCG-3' (SEQ ID NO: 2)), thymosin (forward: 5'-CTGTGAGC-CATCAA-GCTGTTG-3' (SEQ ID NO: 3); reverse: 5'-GGT-GTACATGGCATCCGATTT-3' (SEQ ID NO: 4)), β-tubulin (forward: 5'-AGCCAT-CCTTCTTGGGTATG-3' (SEQ ID NO: 5); reverse: 5'-AGTTTCCCGTCCTTGTTCG-3' (SEQ ID NO: 6)), β-actin (forward: 5'-AGCCATCCTTCTTGGG-TATG-3' (SEQ ID NO: 7); reverse: 5'-ATACCTGGGAA-CATGGTGGT-3' (SEQ ID NO: 8)), and mitochondrial 16S rRNA (forward, 5'-ACCTTGACTGTGCTAAGGTAG-CATAA-3' (SEQ ID NO: 9); reverse, 5'-CAGTTCTTC-CCTAT-TAATCCGTTCAT-3' (SEQ ID NO: 10)). Overall cDNA expression levels per sample were normalized to the expression of 16S rRNA. The relative expression level of the genes of interest was calculated by $\Delta C_T$ methods.

Double-stranded siRNA production and delivery. Caltubin-specific 27-mer siRNAs were designed using SciTools RNAi Design software (IDT DNA). TriFECTa control RNA was used as a control in the experiments (IDT DNA). The siRNA sequences are: caltubin siRNA1 (LCa1) 5'-GAAACUUUCACU UGAUGAAUUCAAG-3' (SEQ ID NO: 11), caltubin siRNA3 (LCa3) 5'-CCACGUUCGAC-GAGGUCAAGAACTA-3' (SEQ ID NO: 12), caltubin siRNA6 (LCa6) 5'-UGGACACUGUCCAGGGUUAUUA-CAT-3' (SEQ ID NO: 13), caltubin siRNA10 (LCa10) 5'-UUAAUGAUGCCAUUGGUUAGAUATA-3' (SEQ ID NO: 14); TriFECTa control 5'-UCACAAGGGAGAGAAAG AGAGGAAGGA-3' (SEQ ID NO: 15). Unless other wise specified, the caltubin siRNA used in the experiments was LCa3.

For whole animal RNA knockdown experiments, snails were anaesthetized with 10% (v/v) Listerine, and 2 μl of 20 μM control siRNA or caltubin siRNA was injected into the head, above the central ganglia using a microlitre syringe (Hamilton Company, Reno, Nev., USA). Ganglia were removed 48 hrs post-injection, and RNA or protein was extracted. The mRNA and protein levels of caltubin were measured using semi-quantitative RT-PCR and Western blotting, respectively, to confirm knockdown. For cultured cells, siRNA (7 nM) was directly applied to culture medium, as described previously (Lu and Feng, 2011).

Neurite outgrowth assays and neurite injury in *Lymnaea* neurons. PeA neurons were cultured in conditioned medium (CM) for 15 hours to allow initiation of outgrowth, and cells with initial neurite lengths between 40 and 60 μm were used. Caltubin siRNA (7 nM) or control siRNA (7 nM) was then applied to culture medium (designated as t=0) and neurite outgrowth was monitored for a period of 30 hours using an Olympus inverted microscope (CK X41) with an Olympus C5050 digital camera. Images were analyzed using ImageTool 3.1 software. The net changes in the neurite lengths were measured at various time points following siRNA application (t=0). Where there were multiple neurites for a given cell, an average length of all neurites belonging to one cell was calculated and counted as one sample. Neurite length was measured from the edge of the soma to the tip of the growth cone.

For neurite injury, PeA cells were cultured in CM for a period of 20 hours to allow for neurite outgrowth, and cells with initial neurite lengths between 70 and 90 μm were used. The neurites were severed using glass micropipettes and then immediately treated with either caltubin siRNA (7 nM) or control siRNA (7 nM) (designated as t=0). Neurite measurements were carried out on the proximal (soma-attached) and distal (free) ends of the transected neurites at various time points, as described above.

Immunocytochemistry and confocal microscopy. Antibodies against caltubin were raised in rat against synthetic peptides corresponding with the N-terminal (MERAFEDVRSQHRDC (SEQ ID NO: 16)) and C-terminal (CDGKLSLDEFKTLYSP (SEQ ID NO: 17)) regions of the protein. Cultured PeA neurons were fixed, permeabilized and incubated with specific primary antibodies (NCS-1: 1:300, Biomol, Cat# BML-NL3750-0100; β-tubulin: 1:300, Sigma, Cat# T0198; α-tubulin: 1:300, Sigma, Cat# T6074; β-actin: 1:300, Sigma, Cat# A1978; and caltubin: 1:200), as described previously (Hui et al., 2007). Cells were then incubated with their respective secondary antibody (488 goat-anti-rat, Chemicon; Alexa Fluo 568 goat-anti mouse, Invitrogen; Alexa Fluo 633 goat-anti-rabbit, Invitrogen) for 2 hours at room temperature. To test for specificity of antibodies, cells were incubated with secondary antibodies only and no signal was observed under these conditions. Unless otherwise specified, immunocytochemistry of PeA neurons was conducted 6-8 hours following siRNA treatment. Confocal images were acquired using a TCS SL laser confocal microscope (Leica Confocal Software, version 2.5, build 1347, Leica Microsystems, Germany), as described previously (Hui et al., 2007). Each Z-plane was 0.5 μm. Background fluorescence was determined in three regions not containing cells throughout the entire z-stack. All siRNA-treated cells were imaged using the same magnification and laser settings. To quantify antibody staining, the mean amplitude fluorescence intensities (arbitrary units, AU) were averaged from sections of the z-stack for each region of interest, and NCS-1 was used as a control against which microfilament intensities were measured. Each bar represents the average protein level from all cells under that condition.

Protein co-Localization analysis. The analysis was conducted to quantify distribution of the proteins labeled with different fluorescence markers and to measure the degree of overlap of the fluorescence signals within the same pixel. Colocalization suggests a high probability of two proteins co-occurring in close proximity. Confocal images of cells double-stained with antibodies for proteins of interest were scanned at a resolution of 1024×1024 pixels in the selected regions of interest (ROI) in the neurites and growth cones of PeA cells, using a 63× oil immersion lens (Leica Microsystems, Germany). Under a zoom of 1, the scan field for each image is 238×238 μm$^2$, and thus each pixel is 0.054 μm$^2$. Growth cone and neurite were scanned at a zoom of 2. Each fluorescence signal was imaged separately with corresponding channels and protein co-localization was estimated based on the degree of overlay between the fluorescence intensities, as measured through analysis of each pixel in the ROI, without pixel saturation. For each image, an ROI was selected in the neurite, growth cone, and an area outside the cell to be used as the control. Using the intensity correlation analysis, a Pearson correlation coefficient was calculated using Image) software (http://rsb.info.nih.gov/ij/), where a coefficient close to 1.0 indicates close co-localization, and 0 indicates low probability for co-localization (also see Li et al., 2004, and Colocalization Module 2007, BioIImaging and Optics).

Western blotting. Protein samples were prepared from snail ganglia, mouse brain, or PC12 cells expressing GFP, caltubin-GFP or caltubin-myc, in RIPA buffer (50 mM Tris-Cl, pH 7.6, 150 mM NaCl, 2 mM EDTA, 1 mM PMSF plus 1% Igepal CA-630, 0.5% sodium deoxycholate, 1% Triton X-100) with a protease inhibitor cocktail (5 μl/100 mg tissue, Sigma), as described previously (Hui et al., 2007). The samples were centrifuged at 4° C. at 13,000 rpm for 15 min. Supernatant was extracted and protein concentrations were measured (Bio-Rad, Hercules, Calif.). Membranes were incubated with rabbit polyclonal anti-rat caltubin antibody (1:500), anti-mouse β-tubulin (1:1,000), anti-mouse α-tubulin (1:6000, Sigma), GFP (1:1,000, Ab6673, Abcam), myc-tag (1:500, 05724, Upstart), β-actin (1:10,000) overnight at 4° C. The membrane was then incubated with appropriate horseradish peroxidase-conjugated secondary antibody accordingly (1:10,000; ImmunoResearch) for 1 hour at room temperature. Antibody-labeled protein bands were visualized using enhanced chemiluminescent reagents (PerkinElmer, Boston, USA), and analyzed by exposure to film (HyBlot CL, USA).

Co-immunoprecipitation (co-IP). As described previously (Fei et al., 2007), snail ganglia protein (300 μg) or PC12 cell protein (250 μg) were incubated with Protein A/G Plus-Agarose beads (Santa Cruz Biotechnology) for 30 min on ice. The cell lysates were centrifuged at 10,000 g for 3 min. The supernatants were collected and then incubated with caltubin primary antibody overnight at 4° C. The protein mix was incubated with Protein A/G Plus-Agarose beads and agitated for 2 hours on ice and then centrifuged again at 10,000 g for 1 min. A sample of supernatant was collected for Western blotting to detect the level of the unbound proteins. The pellet was washed with lysis buffer and centrifuged at 500 g for 1 min, repeated 5 times. The pellet was placed in 40 μl Laemmli buffer (eBioscience; with 50 mM DTT). After vortex, the pellet was boiled for 10 min, and then centrifuged at 10,000 g for 3 min. The supernatant was collected for Western blotting.

Protein affinity purification (pull-down). For affinity pull-down experiments, GST-caltubin fusion protein was prepared as described previously (Jarvis et al., 2002). Full length caltubin cDNA was amplified by PCR and cloned into pGEX4T-1. The construct was re-sequenced to confirm appropriate insertion sites and the absence of spurious PCR generated nucleotide errors. Expression of the transformed plasmid in BL21 (DE3) Bacteria (C2527I, New England BioLabs, MA) was induced by IPTG (isopropyl β-D-1-thiogalactopyranoside, I5502, Sigma, Canada). GST-fusion protein was collected from bacterial lysate and purified using glutathione- Sepharose 4B beads as described by the manufacturer (17-0756-01, GE Healthcare, Sweden). For affinity purification experiments the solubilized protein extracts (300 µg of protein) were incubated overnight at 4° C. with glutathione-Sepharose beads (Pharmacia, Dorval, Quebec, Canada) bound to the indicated GST-fusion proteins (50 µg). Beads were washed three times with 600 µl of PBS containing 0.2% Triton X-100 and bound proteins were eluted with glutathione elution buffer. Eluates were incubated in sample buffer and subjected to 10% SDS-PAGE for Western blot analysis.

PC12 cell culture and transfection. Rat pheochromocytoma PC12 cells were a kind gift from Dr. Shuzo Sugita (University Health Network, University of Toronto), who originally obtained the cells from Dr. Thomas Martin (University of Wisconsin). The cells were maintained on 35 mm poly-L-lysine-coated dishes in a 37° C. maintained in a 9% $CO_2$ incubator in Dulbecco's modified Eagle's medium (DMEM, HyClone) supplemented with 5% Bovine Calf Serum (BCS, HyClone), 5% Donor Equine (DE, HyClone), 200 U/ml penicillin, 0.2 mg/ml streptomycin and 0.25 µg/ml Amphotericin B.

PC12 cells were transfected with caltubin-GFP or GFP plasmid (1-3 µg/ml) using Lipofectamine 2000 (Life Technologies, Inc.). Six hours following transfection, 50 ng/ml of nerve growth factor (NGF, Invitrogen) was added to the culture medium (DMEM). For neurite outgrowth experiments, cells were maintained in culture for 7 days (DIC7). For the neurite injury experiment, neurite crush was induced on day 5 (DIV5) and cells were monitored for 30 hours.

Mouse cortical neuron culture and transfection. All procedures were performed following the animal welfare guidelines at the University of Toronto and were approved by the institutional animal care and use committee. Cortical cultures were prepared from embryonic day 18 (E18) mice following the published protocols (Araki et al., 2001; Hares et al., 2011) with modification. Cerebral cortex was incubated in 0.25% trypsin/EGDA (Invitrogen) for 15 min at 37° C. Neurons were then dissociated, and plated in low density (100,000/ml) on coverslips coated with poly-D-lysine (70-150 kDa, Invitrogen). Cells were maintained in Neurobasal medium with 2% B27 supplement, 1× Penn/Strep, and 2 mM L-glutamine (all from Invitrogen) at 37° C. with 5% CO2. Neurons were transfected with caltubin-GFP or GFP plasmid (1-3 µg/ml) using Lipofectamine 2000 (Life Technologies, Inc.). For neurite outgrowth experiments, cells were transfected on day 1 in culture (DIV1) and maintained for 3 days. For the neurite injury experiment, cells were transfected on DIV 3 and neurite were injured on DIV5.

Statistics. Data are presented as the mean±SEM. Statistical analysis was carried out using SigmaStat 3.0 (Jandel Scientific, Chicago, Ill., USA). The significance of the differences amongst mean values for multiple experimental groups was tested using one-way analysis of variance (ANOVA, Holm-Sidak post hoc comparison). Differences were considered significant when $p<0.05$.

Results

Caltubin Transcript and Protein are Expressed in Neurites and Growth Cones of Cultured PeA Neurons.

Full length cDNA of caltubin was first cloned. Sequencing of a full-length caltubin cDNA predicted a 19 kDa protein with four putative calcium-binding EF-hand motifs (FIG. 1). Sequence alignment with other calcium binding proteins that show highest sequence similarity with caltubin, i.e., the calmodulins and calcineurins, reveals very low overall sequence identity, implicating caltubin as a novel type of putative EF-hand calcium-binding protein.

To study the distribution of caltubin transcript in *Lymnaea* neurons, in situ hybridization was conducted with a caltubin antisense RNA probe, both on pedal ganglia sections and on cultured PeA neurons. In ganglia sections, abundant expression of caltubin mRNA was detected by the caltubin antisense probe in neuronal cell bodies (dark regions) as well as in neurites in the neuropil, whereas the sense control RNA probe showed negative in these experiments indicating the specificity of the RNA probe. In cultured PeA neurons, a strong presence of caltubin mRNA was detected in neuronal somata, and in localized regions of neurites and growth cones by caltubin antisense probe but not by caltubin sense probe. The high power image showed that caltubin transcript was unevenly distributed in neurites and accumulated in specific regions. Real-time qPCR analysis confirmed that caltubin mRNA was expressed in isolated neurites in culture. After 2 days in culture, the cell bodies were removed and mRNA was extracted from the cell bodies and from neurites separately. Real-time qPCR analysis was carried out to measure the transcript levels of caltubin and two other known neuritic transcripts, β-thymosin and β-tubulin, as positive controls. All mRNA levels were first normalized to the level of 16S rRNA, and neuritic mRNA levels were then divided by somatic mRNA levels. It was found that caltubin mRNA level was approximately 6-fold higher in the neurites than in the cell somata. The neuritic/somata expression ratio of caltubin mRNA was higher than that of β-thymosin and β-tubulin (the positive controls). These data further confirm that caltubin mRNA is indeed present at high levels in neurites. To study neuronal caltubin protein expression, antibodies were generated against the C-terminus and N-terminus of the protein. Immuno-blotting showed that all antibodies recognized a single protein band with an apparent MW of ~20 kDa corresponding to the predicted molecular weight of caltubin. Confocal immunofluorescence imaging revealed caltubin immunoreactivity in the soma, neurites and growth cones of cultured PeDI neurons.

Expression/Local Synthesis of Caltubin Required for Neurite Outgrowth/Regeneration of Adult PeA Neurons An RNA interference approach was used to study the role of caltubin in cultured PeA neurons. Previous studies demonstrated that short siRNAs can be used for efficient gene silencing in cultured *Lymnaea* neurons. It was shown that caltubin-specific siRNAs effectively knocked down caltubin mRNA (FIG. 2A) and protein levels, both in intact ganglia in vivo (FIG. 2B) and in cultured PeA neurons in vitro (FIG. 2C) 6 hours after siRNA application. Three siRNAs targeting 3 different regions of the caltubin gene were tested and all resulted in a significant decrease in protein levels (FIG. 2B). Caltubin levels measured in cultured PeA neurons progressively decreased over time in caltubin-siRNA (LCa3) treatment cells, but not in control siRNA treated cells (FIG. 2D). Caltubin knockdown reached 30% reduction at 3 hours (0 hr: 1.92±0.09, n=11; 1.5 hrs: 1.74±0.07, n=11; 3 hrs: 1.19±0.13, n=9, $p<0.05$), and 50% reduction at 6 hours (0.81±0.06, n=10; $p<0.05$), which was similar to that observed at 24 hours.

Figure 3:
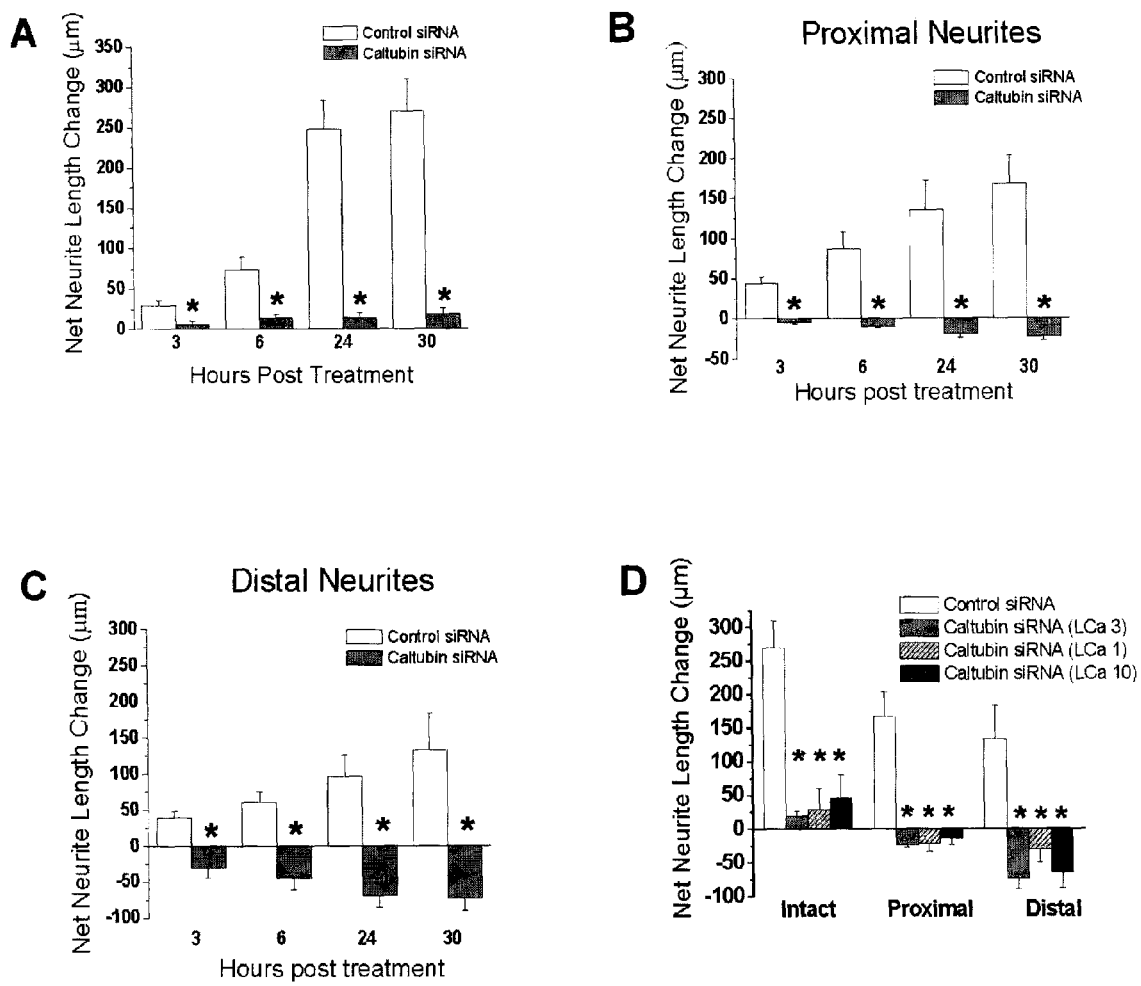
FIG. 3 graphically illustrates that caltubin-siRNA treatment severely disrupts neurite extension of cultured adult PeA neurons (A), that caltubin is required for post-injury regeneration of soma attached PeA proximal (B) and distal (C) neurites in culture, and that caltubin-siRNAs targeting different regions of the transcript were effective to prevent neurite outgrowth (D)

To elucidate the function of caltubin in neurite outgrowth, neurite extension of cultured PeA neurons was compared in the presence of either caltubin siRNA or control siRNA. PeA neurons were cultured for 15 hours to allow initiation of outgrowth, and cells with an initial outgrowth of 40-60 µm were used for further analysis. Caltubin siRNA or control siRNA were added in the culture medium at t=0, and neurite outgrowth was monitored for 30 hours thereafter. Interestingly, a large difference in the outgrowth between the two groups was observed over this period. Neurites of control siRNA treated cells grew 268.9±40 µm (n=17) on average, which was significantly longer than neurites of caltubin siRNA group (19±7 µm, n=26; p<0.05) (FIG. 3A). These results indicate that caltubin-siRNA treatment severely disrupts neurite extension of cultured adult PeA neurons. These findings indicate that caltubin is involved in neurite regeneration.

To test the potential role of caltubin in neurite regeneration of PeA neurons, axotomy (neurite transection) was applied to cultured PeA cells, and then the growth capacity of both the proximal (soma-attached) neurite and the distal (disconnected) neurite was measured following treatment with either control siRNA or caltubin siRNA. Specifically, PeA neurons were maintained in culture for 20 hours, and cells containing neurites with lengths of approximately 70 µm were utilized. Neurites were severed using a glass micropipette and immediately treated with either control siRNA or caltubin siRNA. Neurite measurements were carried out over a period of 30 hours following injury. As expected, the growth of injured neurites was severely inhibited by caltubin-siRNA. For proximal injured neurites, a net elongation of 168±35 µm (n=7) was observed in control siRNA condition; in contrast, a net retraction of 23±4 µm (n=6) was observed under the caltubin siRNA condition over the same 30 hour period (p<0.05; FIG. 3B). These data indicate that caltubin is required for post-injury regeneration of soma attached PeA neurites in culture. Similar to proximal neurites, the distal neurites of axotomized PeA neurons treated with control siRNA also showed a net increase in neurite length (133±5 µm; n=10) over a 30 hour period, whereas the distal neurites of cells treated with caltubin siRNA experienced a net retraction of 73±17 µm (n=18) over the same period (p<0.05; FIG. 3C). It is worth noting that all the axotomized neurites were treated with siRNA after the injury, and the differences observed in the isolated (distal) neurites between control and caltubin siRNA treatments over 30 hours were likely a result of locally synthesized proteins, which were suppressed by caltubin siRNA. To confirm the specificity of caltubin knockdown, cells were treated for 30 hours with each of three caltubin-siRNAs targeting different regions of the transcript. It was found that all three siRNAs consistently reduced the outgrowth ability of the intact neurites and caused substantial retraction in the injured neurites (FIG. 3D). These observations indicate that caltubin is an important protein for normal neurite development.

Caltubin Regulates β-Tubulin but not β-Actin Protein Levels in PeA Neurites

Figure 4:
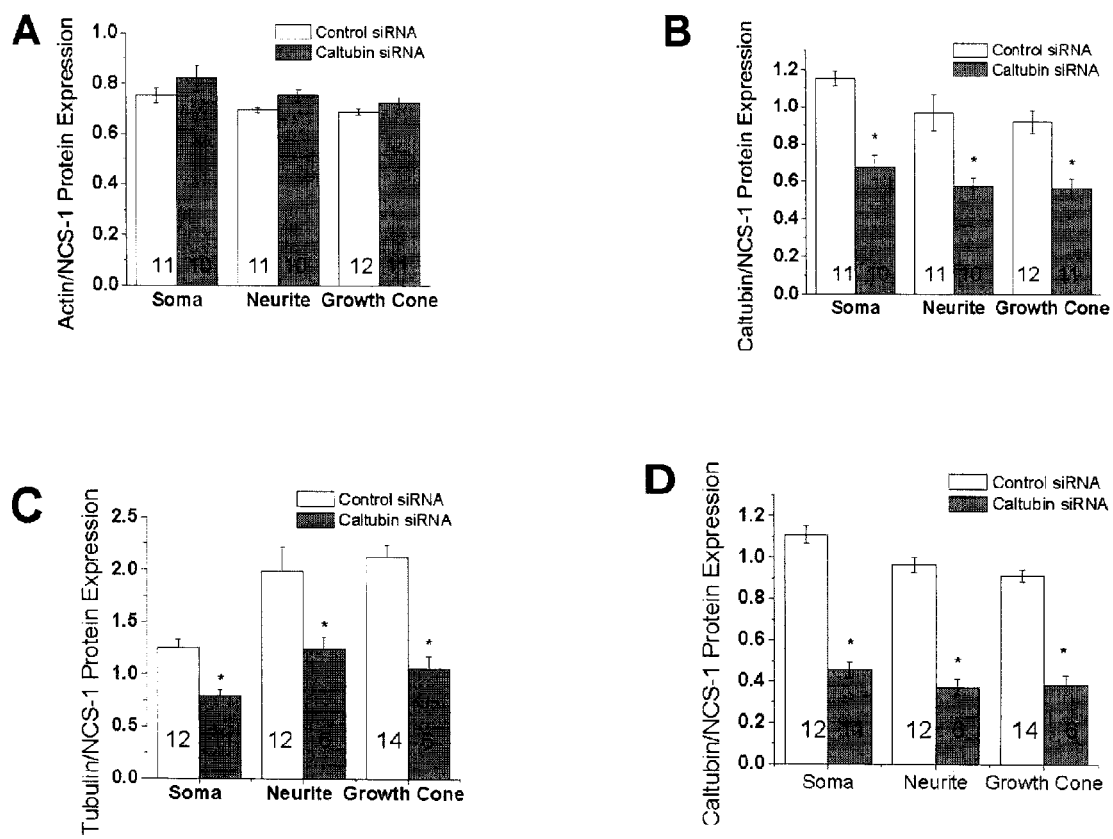
FIG. 4 graphically illustrates that knockdown of caltubin reduces β-tubulin protein levels (C) and caltubin levels (B/D) but not β-actin (A) in PeA cells treated with control or caltubin siRNA.

Neurite outgrowth and maintenance are highly dependent on the proper assembly of actin and tubulin and can be regulated by calcium-binding proteins. Whether or not caltubin affects neurite outgrowth and regeneration by regulating actin or tubulin expression was investigated. Immunocytochemical triple-labeling of caltubin, neuronal calcium sensor 1 (NCS-1), and β-actin or β-tubulin in cultured PeA cells treated with either control siRNA or caltubin siRNA was then conducted. NCS-1 was used as a reference protein. Protein expression levels of β-actin and NCS-1 in the soma, neurites and growth cones of PeA neurons were found not to be significantly different between control siRNA (n=11, 11, 12) and caltubin siRNA (n=10, 10, 11) treated cells (FIG. 4A), whereas the relative level of caltubin to NCS-1 was significantly reduced (FIG. 4B). These data are consistent with the immuno-blot analysis, which showed that global β-actin levels did not vary with caltubin siRNA treatment. In contrast, the relative β-tubulin protein levels in caltubin siRNA treated cells were significantly reduced by 45±2.7% (n=11; p<0.05) in the soma, 34±5.8% (n=6; p<0.05) in the neurite, and 30±9.7% (n=6; p<0.05) in growth cones compared with control siRNA treated cells (n=12, 12, 14) (FIG. 4C), corresponding with a significant decrease in caltubin level (FIG. 4D). Taken together, these data demonstrate that caltubin has a differential effect on the expression of cytoskeletal proteins. Knockdown of caltubin specifically reduced β-tubulin protein levels, without affecting β-actin protein levels, indicating that caltubin's effect on neurite outgrowth and regeneration may be, at least in part, through the regulation of β-tubulin levels.

Neurite Outgrowth of PeA Cells Requires Local Synthesis of Caltubin

Three lines of evidence suggested that caltubin might be synthesized locally in growth cones: (1) caltubin transcripts were present in neurites, (2) caltubin-siRNA reduced the caltubin level in growth cones, and (3) isolated (distal) neurites treated with caltubin-siRNA after the injury showed retraction, in contrast to those treated with control siRNA, which showed elongation. Because the distal neurites no longer received proteins transported from cell somata, the proteins required for outgrowth of the isolated neurites were likely synthesized locally. Caltubin-siRNA reduced caltubin level in growth cones, which may be a result of interruption of the local synthesis of caltubin. To test this hypothesis, the relative levels of caltubin over NCS-1 (as a control) in axotomized neurites of the PeA neurons was measured either immediately or 3 hours following injury. The levels of caltubin in both distal (FIG. 5A) and proximal (FIG. 5B) neurites increased significantly within 3 hours following injury (Distal: 0 hr: 0.56±0.05, n=8; 3 hrs: 0.71±0.05, n=7; p<0.05. Proximal: 0 hr: 0.45±0.03, n=8; 3 hrs: 0.72±0.05, n=7; p<0.05). The increase in caltubin levels in distal neurites indicates that the pro-regenerative effects of caltubin are, at least in part, derived through local synthesis of caltubin.

Figure 5:
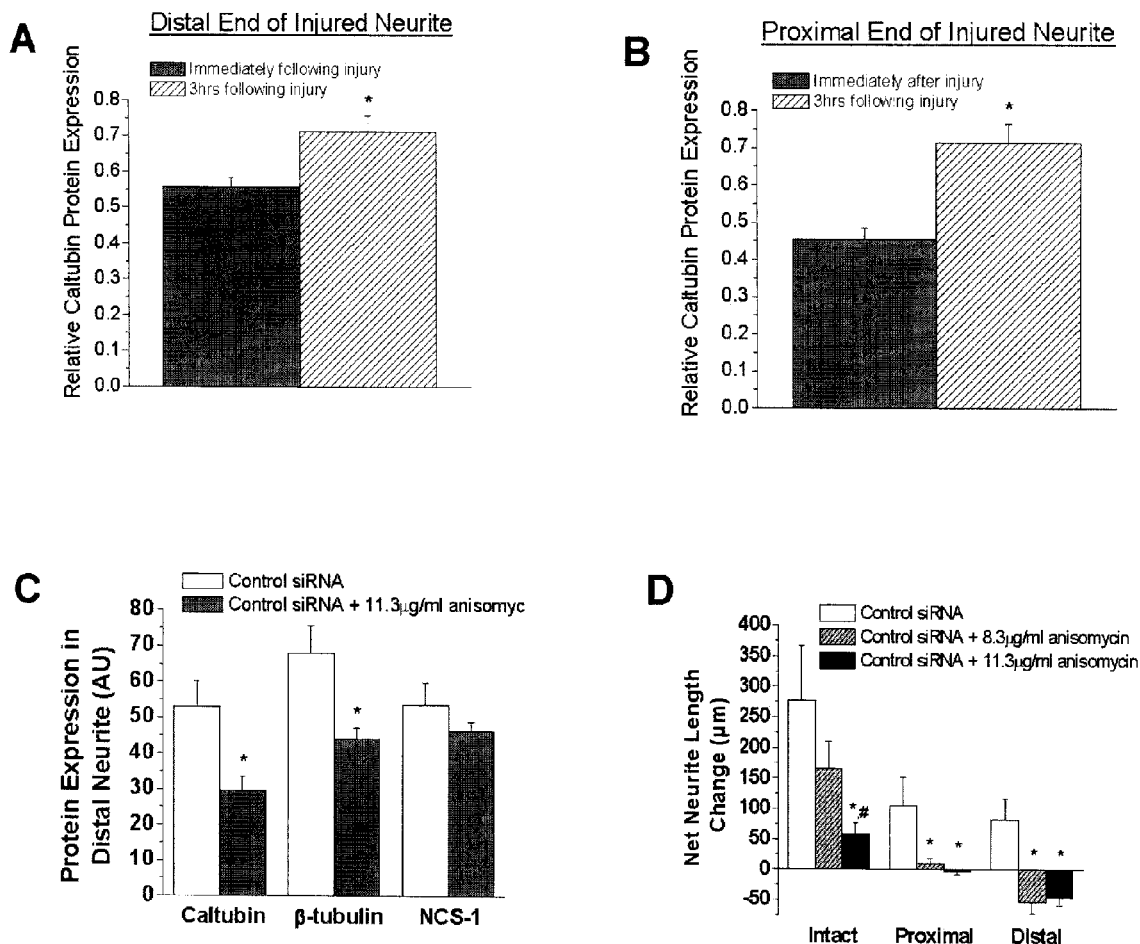
FIG. 5 graphically illustrates that injury increases caltubin protein levels in distal (A) and proximal (B) neurite portions, and also illustrates the expression levels of caltubin, β-tubulin and NCS-1 in distal neurites (C) treated with the protein translation inhibitor, anisomycin, as well as the lengths of the intact neurites, and of proximal and distal ends of axotomized neurites (D) after the treatment.

To confirm that axotomized neurites indeed synthesize caltubin locally, the expression of caltubin, β-tubulin, and NCS-1 in distal regions of transected neurites, was compared in the presence or absence of a protein translation inhibitor, anisomycin (11.3 µg/ml). It was found that both caltubin and β-tubulin protein levels, but not NCS-1 protein levels were significantly reduced in distal neurites 30 hours following anisomycin treatment as compared with the control (FIG. 5C). Outgrowth of the intact neurites and the severed neurites following axotomy was suppressed and the retraction of severed neurites was observed in the presence of anisomycin (FIG. 5D). These observations further support the notion that neurite outgrowth/regeneration in cultured *Lymnaea* PeA neurons required local translation of caltubin in the distal regions of the neurite.

Figure 6:
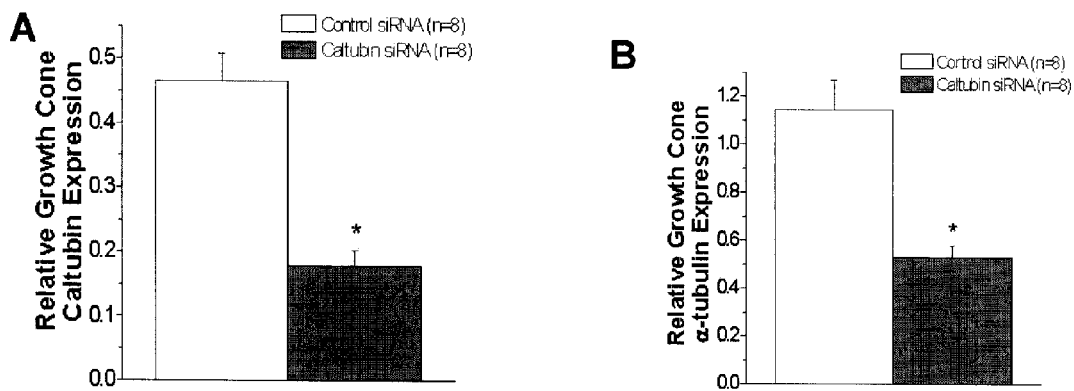
FIG. 6 graphically illustrates that knockdown of caltubin in PeA neurons reduces caltubin (A) and α-tubulin levels (B) against NCS-1.

Caltubin Co-Localizes and Interacts with Tubulin but not β-Actin in *Lymnaea* Neurons To further explore the mechanism of β-tubulin regulation by caltubin, the degree of spatial colocalization between caltubin and β-tubulin was tested using confocal immunofluorescence intensity correlation analysis. Protein colocalization suggests a high probability of two proteins co-occurring in close proximity. Co-localization was evaluated by measuring the level of overlap between signal intensities of the corresponding fluorescent channels over the selected pixels in randomly selected regions of PeA neurites and growth cones. PeA cells previously treated with control siRNA were double-labeled for caltubin and either β-tubulin, β-actin or NCS-1. Co-localization of proteins in neurites and/or growth cones was estimated based on the Pearson correlation coefficient: a coefficient (Rr) close to 1 indicates co-localization, while a coefficient close to 0 indicates no co-localization (Li et al., 2004). The data show that caltubin is co-localized with β-tubulin in neurites and growth cones (neurites: Rr=0.67±0.08, n=6; growth cones: Rr=0.75±0.10, n=6). In contrast, a much lower correlation was found between caltubin and β-actin, (Rr=0.12-0.20) and between caltubin and NCS-1 (Rr=0.18-0.30), indicating that there was a low probability for co-localization between caltubin and β-actin or NCS-1. Protein colocalization only implies a high probability of two proteins occurring together in a specific region. Thus, to further determine whether the colocalized proteins physically interact, a series of immunoprecipitation (IP) or affinity pull-down analyses were conducted. It was found that caltubin bound to β-tubulin, but not to β-actin, and not in the negative control IPs. Interestingly, caltubin binding to α-tubulin was also observed. To further investigate whether caltubin also regulates α-tubulin levels in growth cones, triple immunocytochemical staining was used. Similar to β-tubulin, relative α-tubulin protein levels in growth cones of caltubin siRNA treated cells were significantly reduced (0.53±0.05, n=8) as compared with control siRNA treated cells (1.14±0.13, n=8; p<0.05) (FIG. 6B), and corresponded with a significant decrease in caltubin levels (caltubin siRNA: 0.18±0.024, n=8; control siRNA: 0.47±0.042, n=8; p<0.05) (FIG. 6A). Taken together, these results indicate that caltubin co-localizes and interacts with tubulins in *Lymnaea* neurons, and point to a direct mechanism in the regulation of microtubule proteins by caltubin.

Caltubin Interacts with β-Tubulin; Promotes Axon Elongation; Attenuates Neurite Retraction of PC12 Cells Since tubulins are highly conserved during evolution, the mechanism of β-tubulin regulation by caltubin in mammalian cells was tested. The potential binding between caltubin and β-tubulin was tested in rat PC12 neurons by conducting co-immunoprecipitation experiments on cultured PC12 cells, which had been transfected with caltubin-myc, caltubin-eGFP or eGFP only (each construct at 3 μg/ml) and allowed a period of 3 days for growth. The Western blot data show that β-tubulin was present in all three input samples, however, the relative levels of β-tubulin in caltubin-expressing cells over GFP-expressing cells significantly increased (caltubin-GFP: 1.17±0.07; caltubin-myc: 1.12±0.04; n=4; p<0.05). In immunoprecipitated samples, β-tubulin was detected in protein complexes obtained from PC12 cells transfected with caltubin-eGFP and caltubin-myc, but not from cells transfected with only eGFP. To confirm these findings, the level of unbound β-tubulin remaining in the supernatant collected following immunoprecipition assay was measured. It was found that the level of unbound β-tubulin remaining in the supernatant of the eGFP-transfected cells was higher than that in the supernatant of the caltubin-eGFP and caltubin-myc transfected cells, consistent with the IP data. These experiments indicate that in mammalian cells, the ability of caltubin to bind to β-tubulin is conserved.

Figure 7:
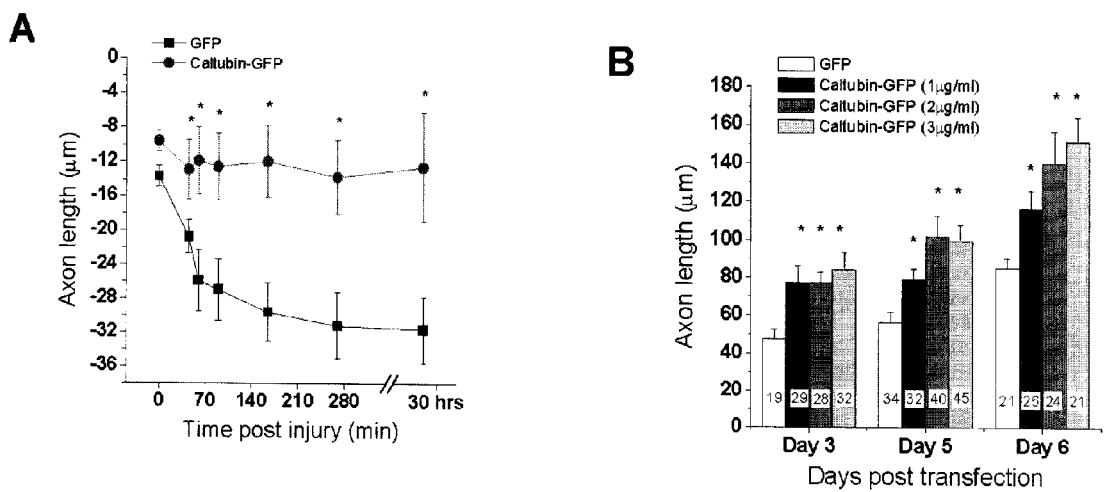
FIG. 7 graphically illustrates that caltubin expression in rat PC-12 cells promotes axonal elongation (A) and attenuates axonal degeneration (B)

Next, the ability of caltubin to influence axonal elongation in PC12 cells was tested. Cells were transfected with either 1 μg/ml, 2 μg/ml or 3 μg/ml caltubin-eGFP construct or 3 μg/ml eGFP control construct, and NGF was added on the first day following transfection. Consistent with previous reports, PC 12 cells extended processes following NGF exposure and were capable of axonal elongation for up to 10 days in culture. Overexpression of caltubin-eGFP prevented significant axon retraction (FIG. 7A) and significantly increased axon extension compared with the eGFP only controls, in a time-dependent and dose-dependent fashion (FIG. 7B). Specifically, following transfection, the axons of control cells expressing eGPF extended over time in culture (3 days: 47.34±5.1 n=19; 5 days: 56.31±5.9 n=34; and 6 days: 85.4±5.1 μm, n=21). The axons of cells treated with caltubin-eGFP (1 μg construct) extended significantly longer (3 days: 77±9.1 μm, n=29; 5 days: 79±5.8 n=32; and 6 days: 116.4±9.3 μm, n=26; p<0.05), as compared to the controls. The increase in axonal extension was also observed at higher caltubin-eGFP concentrations (2 and 3 μg).

To determine whether or not caltubin affects axonal degeneration following axotomy in PC12 neurons, caltubin-eGFP (3 μg/ml) or eGFP alone was expressed and processes were allowed to grow for a period of 5 days. Cells with initial axons of approximately 70 μm were identified and marked for time-lapse imaging. Axons were injured by cutting off the growth cone using a glass micropipette, and axonal behavior was monitored over various time points following the injury. At 45 minutes after the procedure, injured axons of cells transfected with eGFP alone showed a significant net retraction of 20.72±1.94 (n=19), whereas axons of cells transfected with caltubin-eGFP showed a net retraction of only 12.89±3.45 μm (n=15) (p<0.05). The axons in the eGFP-only group continued to retract over the next 24 hours (total net retraction of 31.62±3.9 μm; n=19), whereas axons expressing caltubin-eGFP remained stable over the same period of time (total net retraction of 12.62±6.4 μm; n=15) (p<0.05). Taken together, these results demonstrate that caltubin can interact with endogenous mammalian β-tubulin to promote NGF-induced outgrowth and prevent retraction of neuron-like processes following injury in mammalian cells.

Caltubin Interacts with Tubulin; Promotes Axonal Elongation; Attenuates Axonal Retraction of Mouse Cortical Neurons To confirm that caltubin indeed has a conserved role in mammalian neurons, the ability of caltubin to bind to tubulin and promote neurite outgrowth in mouse cortical neurons was tested. Affinity pull-down assays showed that GST-caltubin fusion protein, not GST, precipitated with both β- and α-tubulin, indicating that caltubin binds to mouse microtubule proteins. Caltubin-eGFP was then expressed in neonatal cortical neurons on the first day in culture (DIV 1), and neurite lengths of neurons expressing either eGFP or caltubin-eGFP at DIV3 were measured. Neurons expressing caltubin-eGFP had significantly longer average neurite lengths (186 μm±11, n=24) compared to neurons expressing eGFP only (115±6, n=31; p<0.05) (FIG. 8A), indicating that the snail protein caltubin enhances the growth capability of the mouse neurons. To test whether caltubin also has an effect on neurite regeneration/degeneration, neurons at DIV3 were transfected and the growth cone of one of the neurites at DIV5 was cut through. The net changes in neurite length for a period of 8 hours following injury (FIG. 8B) was then measured. It was observed that cells expressing caltubin-eGFP were able to maintain their neurite length following injury over the 8-hour period (8 hours: −5.11 μm±7.4, n=24), whereas those expressing eGFP only showed neurite retraction (8 hours: −58.38 μm±10.1, n=25. p<0.05). These data confirm that caltubin serves to promote neurite outgrowth and attenuate neuronal retraction in mammalian neurons, where it is normally not expressed.

Example 2

Caltubin-Tubulin Interaction Domains

Figure 9A:
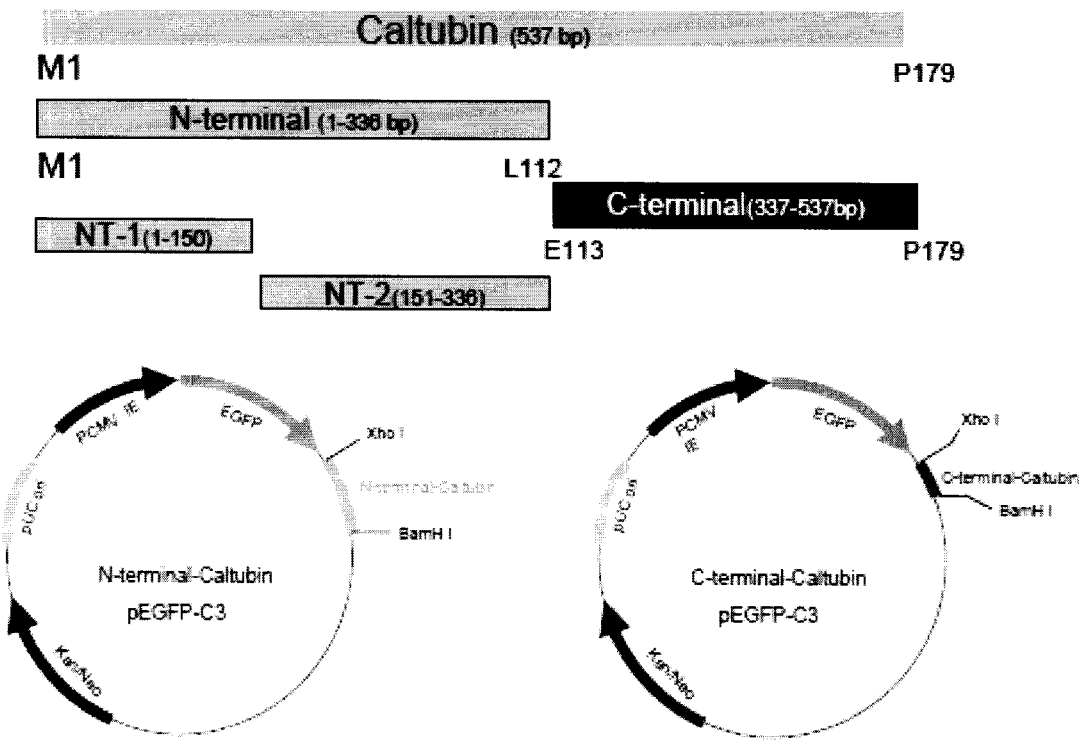
FIG. 9 is a schematic of truncated caltubin peptides (A) and a graph illustrating that NT caltubin enhances outgrowth of hippocampal neurons (B)
Figure 9B:
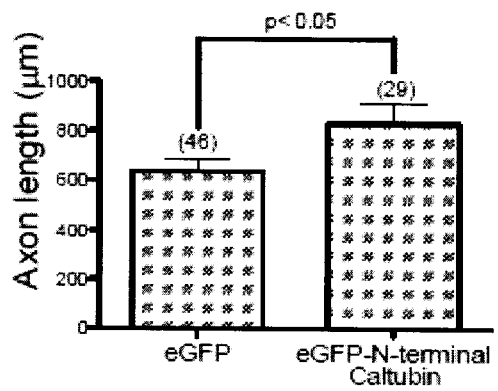

To identify the essential binding domains between caltubin and α- or β-tubulin, a number of reduced GST-caltubin constructs have been created including the N-(NT) and C-terminal (CT) truncates (FIG. 9A). Structure-function analysis in combination with co-IP as described in Chao et al., *J Mol. Cell Cardiol*. (2011), was used to determine binding of the constructs to tubulin. Full-length or truncated caltubin plasmid was amplified by PCR and cloned in pGEX4T-1. Expression of transformed plasmid in BL21 (DE3) bacteria was induced by IPTG. The GST-caltubin fusion protein/peptide was collected from bacterial lysate and purified using glutathione-Sepharose 4B beads (GE healthcare). For co-IP assay, the solubilised protein extracts were incubated overnight at 4° C. with glutathione-Sepharose beads (GE healthcare) bound to 50 µg GST-caltubin fusion protein/peptide. Following washes, bound proteins were eluted with glutathione elution buffer and eluates were subjected to 10% SDS-PAGE for Western blot analysis. It was determined that both the NT and CT caltubin truncates bind to α-tubulin under control conditions; however, only the NT truncate binds to α-tubulin in high calcium conditions (2 mM).

In addition, to determine whether or not the caltubin and caltubin truncates promote axonal elongation, these peptides were introduced to mouse neuronal cell culture using non-viral transfection methods as described in Nejatbakhsh (*J Neurosci*. 31(43), 15231 (2011)). Full-length or truncated caltubin-eGFP or eGFP plasmid (1-3 µg/ml) was mixed with Lipofectamine 2000 (Invitrogen) and added in cell culture. Caltubin (positive control), reduced caltubin plasmids, eGFP only (negative control) were used.

It was found that transfection using the NT (1-336 bp) caltubin plasmid (eGPF-tagged) (FIG. 9A) enhanced outgrowth of mouse hippocampal neurons (FIG. 9B), indicating that the functional domain of caltubin is in the N-terminus of the protein.

EXAMPLE 3

Cell-Penetrating Caltubin and Caltubin Peptides

Figure 10A:
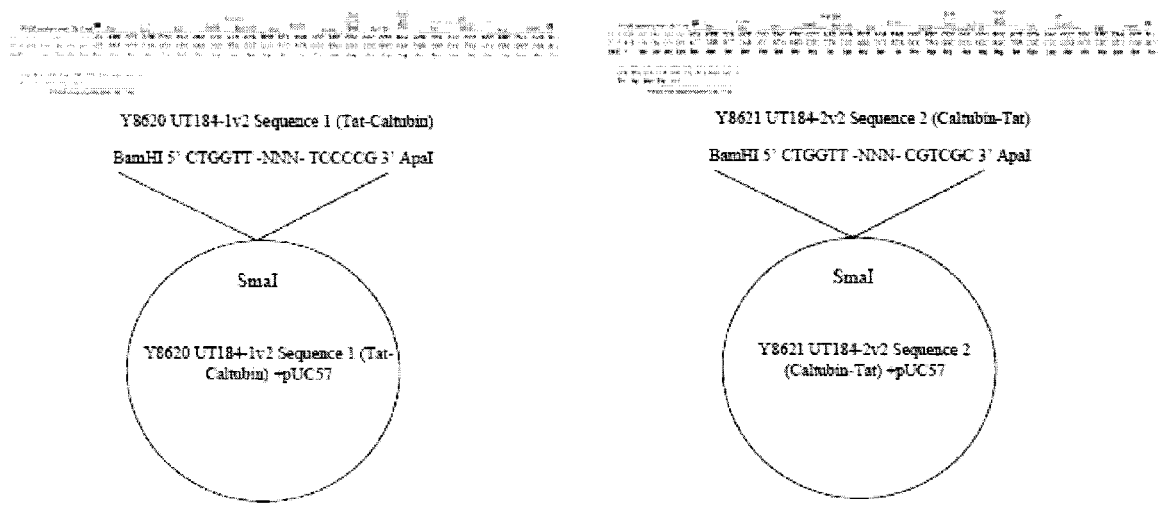
FIG. 10 is a schematic of constructs encoding the TAT-caltubin and the TAT-caltubin peptides (A), and graphically illustrates that TAT-caltubin peptides enters neurons and neurites (B)

In order to increase the efficiency of caltubin peptide delivery, cell-penetrating caltubin protein and peptides were prepared. Specifically, the caltubin peptides linked to the non-toxic HIV-TAT-tag (9 arginine residues) were prepared. puC57 plasmids encoding HIV Tat-linked caltubin were purchased from Bio Basic Canada, Inc. (Markham, Canada). Codons were optimized for expression of the protein in *E. Coli*. Primers (Forward-5'-GACGACGACAAGATGCTG-GTTCCTCGTGGTTGG-3' (SEQ ID NO: 20); Reverse-5' GAGGAGAAGCCGGTTAGCGACGACGTTTCTTACG-3' (SEQ ID NO: 21)) were used to subclone caltubin into the pET-46 Ek/Lic vector (Novagen, Damstadt, Germany) according to the manufacturer's instructions. The resultant plasmid was transformed into the XL-1 Blue competent cells (Stratagene, Santa Clara, Calif., USA) for subsequent amplification and purification. The sequence was then verified and the final cDNA encoded the following peptide sequence: His-6 tag (MAHHHHHH (SEQ ID NO:22), linker region (VDDDDKM (SEQ ID NO:23)), thrombin cleavage site (LVPRGS (SEQ ID NO: 24)), linker region (GA), caltubin (179 aa) (or truncated caltubin) and HIV TAT protein transduction domain (YGRKKRRQRRR (SEQ ID NO: 25)). The plasmid was transformed into *E. coli* BL21 cells and protein expression was induced with isopropylthiogalactoside for 20 hours at 18° C. The fusion protein was purified on a nickel column and then verified by Coomassie blue staining and Western blot analysis. The resulting fusion proteins were dialyzed twice against PBS using the 10K Dialysis Cassette (Pierce, Rockford, Ill.). The proteins either with or without thrombin digestion were then stored in 10% glycerol/PBS at 80° C. until use. Constructs encoding the TAT-caltubin and the TAT-caltubin peptides, including the N-terminal peptide (including amino acid residues 1-336) and C-terminal peptide (including amino acid residues 337-537) (indicated as caltubin-TAT) are shown in FIG. 10A. The sequences of each are shown in FIG. 10B.

Non-purified caltubin-TAT peptide entered mouse hippocampal neurons and their neurites with high efficiency.

EXAMPLE 4

The Effect of Caltubin on Human Cells

It was then confirmed that caltubin enhances outgrowth of human cells. Neuronal cells, HCN-2 (ATCC No. CRL-10742) cells, were used for the experiment. The HCN-2 cells were maintained in culture in DMEM for 7 days and NGF (40 ng) for one day prior the treatment. The cells were then treated with vehicle (PBS) or caltubin-TAT protein (1 µM) in culture for 3 and 5 days.

Figure 11:
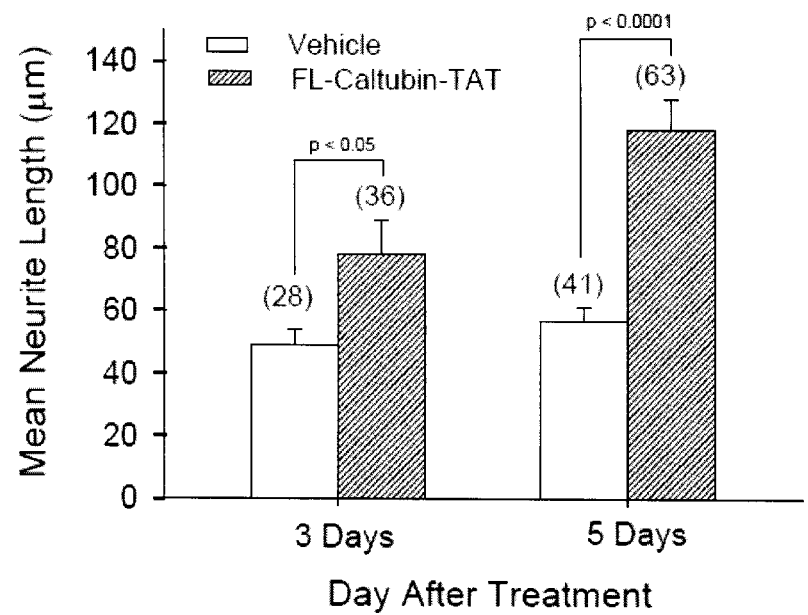
FIG. 11 graphically illustrates neurite length in human cortical neurons following treatment with caltubin.

Mean neurite length was calculated as the quotient of the sum of neurite length from a neuron divided by the number of neurite branches off the neuron. The neurites were measured from all neurons differentiated under the indicated conditions. The number of neurons and the neurite length of the neurons in the caltubin-TAT-treated dish were greater than those under control conditions as shown in FIG. 11. Thus, the Caltubin-TAT protein enhanced differentiation and outgrowth of human cortical neurons (HCN-2, ATCC) in a low density culture.

EXAMPLE 5

The Effect of Caltubin In Vivo

Figure 12A:
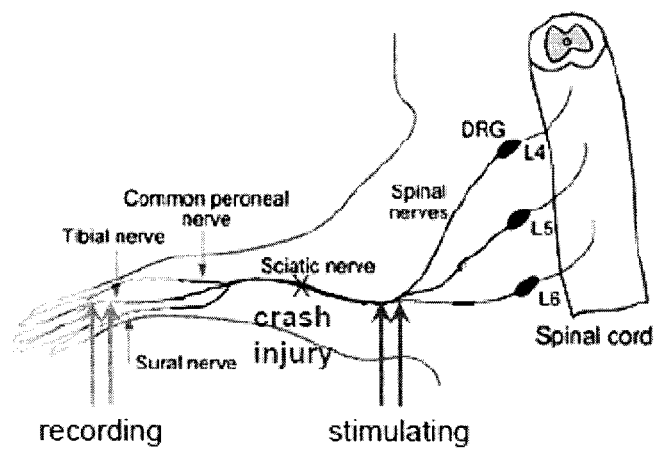
FIG. 12 is a schematic of sciatic nerve injury model (A) and a graph illustrating a trend of enhanced nerve conductance (CAMP in mV) on caltubin treatment in vivo (B).

An in vivo sciatic nerve injury model (Hoke et al. Exp. Neurol. 172(2), 398-406 (2001)) was used to determine the effect of caltubin in vivo. A schematic of the model used is shown in FIG. 12A. Following sciatic nerve crush injury, caltubin-TAT-His6 protein (4 µl of 2.6 µg/µl in PBS) was applied locally and immediately after crush. The control was treated with PBS. The sciatic nerve was isolated and fixed 20 min after CaT-TAT-His6 protein application. Confocal imaging using anti-His6 antibody confirmed entry of caltubin-TAT-protein to mouse sciatic nerve following caltubin application locally.

Figure 12B:
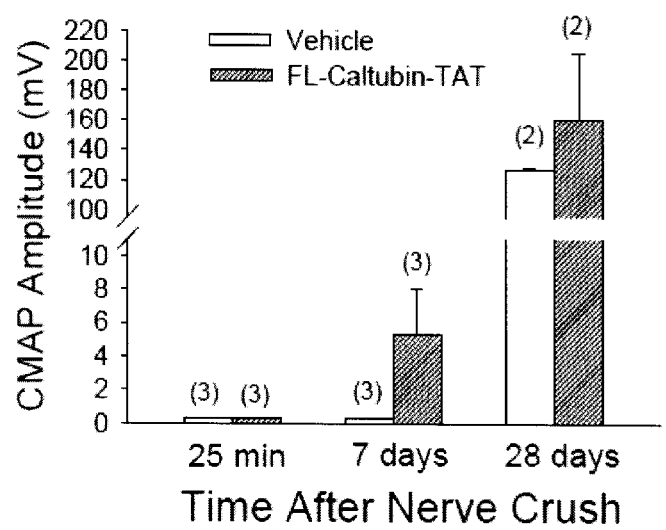

To confirm caltubin results in nerve growth, a single dose (50 µl of 2.6 µg/ul) of full-length caltubin-TAT protein was applied immediately after nerve crush. The compound action potentials were recorded at 25 minutes, 7 days and 28 days. Recording data (CMAP amplitude) confirmed that caltubin enhanced nerve conductance, indicating nerve fibre regeneration, in the early stage of recovery, as shown in FIG. 12B.

The relevant portions of references referred to herein are incorporated by reference.

REFERENCES

Araki T, Nagarajan R, Milbrandt J (2001) Identification of genes induced in peripheral nerve after injury. Expression profiling and novel gene discovery. J Biol Chem 276: 34131-34141.

Fei G, Guo C, Sun H S, Feng Z P (2007) Chronic hypoxia stress-induced differential modulation of heat-shock protein 70 and presynaptic proteins. J Neurochem 100:50-61.

Feng Z P, Klumperman J, Lukowiak K, Syed N I (1997) In vitro synaptogenesis between the somata of identified *Lymnaea* neurons requires protein synthesis but not extrinsic growth factors or substrate adhesion molecules. J Neurosci 17:7839-7849.

Gardzinski P, Lee D W, Fei G H, Hui K, Huang G J, Sun H S, Feng Z P (2007) The role of synaptotagmin I C2A calcium-binding domain in synaptic vesicle clustering during synapse formation. J Physiol 581:75-90.

Hares K, Kemp K, Gray E, Scolding N, Wilkins A (2011) Neurofilament dot blot assays: Novel means of assessing axon viability in culture. J Neurosci Methods.

Hui K, Fei G H, Saab B J, Su J, Roder J C, Feng Z P (2007) Neuronal calcium sensor-1 modulation of optimal calcium level for neurite outgrowth. Development 134:4479-4489.

Jarvis S E, Barr W, Feng Z P, Hamid J, Zamponi G W (2002) Molecular determinants of syntaxin 1 modulation of N-type calcium channels. J Biol Chem 277:44399-44407.

Li Q, Lau A, Morris T J, Guo L, Fordyce C B, Stanley E F (2004) A syntaxin 1, Galpha(o), and N-type calcium channel complex at a presynaptic nerve terminal: analysis by quantitative immunocolocalization. J Neurosci 24:4070-4081.

Lu T Z, Feng Z P (2011) A sodium leak current regulates pacemaker activity of adult central pattern generator neurons in *lymnaea stagnalis*. PLoS One 6:e18745.

Roche F K, Marsick B M, Letourneau P C (2009) Protein synthesis in distal axons is not required for growth cone responses to guidance cues. J Neurosci 29:638-652.

Smit A B, Spijker S, van M J, Burke J F, De W F, Van E R, Geraerts W P (1996) Expression and characterization of molluscan insulin-related peptide VII from the mollusc *Lymnaea stagnalis*. Neuroscience 70:589-596.

We claim:

1. An isolated caltubin protein which exhibits axon regenerating activity, said protein comprising the amino acid sequence of SEQ ID NO: 18, or a functionally equivalent N-terminal fragment of SEQ ID NO: 18 comprising at least amino acid residues 80-112 of SEQ ID NO: 18, or a functionally equivalent variant of said protein or fragment that exhibits at least about 90% homology thereto, wherein the protein, fragment, or variant is linked to a cell-penetrating peptide.

2. The caltubin protein of claim 1, wherein the cell-penetrating peptide is selected from the group consisting of an arginine-rich peptide, an HIV-TAT peptide, vascular endothelial-cadherin, transportan, penetratin, Pep-1 peptide and fragments or derivatives thereof.

3. An isolated polynucleotide encoding a caltubin protein, said protein comprising the amino acid sequence of SEQ ID NO: 18, or a functionally equivalent N-terminal fragment of SEQ ID NO: 18 comprising at least amino acid residues 80-112 of SEQ ID NO: 18, or a functionally equivalent variant of said protein or fragment that exhibits at least about 90% homology thereto, wherein the protein, fragment, or variant is linked to a cell-penetrating peptide.

4. A vector incorporating a polynucleotide as defined in claim 3.

5. A composition comprising a caltubin protein, fragment, or variant as defined in claim 1 and a pharmaceutically acceptable carrier.

* * * * *